(12) United States Patent
Liou et al.

(10) Patent No.: US 7,481,994 B2
(45) Date of Patent: Jan. 27, 2009

(54) CALCIUM BIOSENSOR POLYPEPTIDES AND METHODS OF USE

(75) Inventors: Jen Liou, Mountain View, CA (US); Tobias Meyer, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 46 days.

(21) Appl. No.: 11/446,010

(22) Filed: Jun. 2, 2006

(65) Prior Publication Data

US 2006/0286605 A1 Dec. 21, 2006

Related U.S. Application Data

(60) Provisional application No. 60/688,807, filed on Jun. 8, 2005, provisional application No. 60/688,625, filed on Jun. 7, 2005.

(51) Int. Cl.
*A61B 5/00* (2006.01)
*G01N 33/52* (2006.01)
*C07K 14/00* (2006.01)

(52) U.S. Cl. .................. 424/9.6; 435/7.1; 435/69.1; 435/69.7; 530/350; 536/23.5

(58) Field of Classification Search ................ 435/69.1; 800/8
See application file for complete search history.

(56) References Cited

U.S. PATENT DOCUMENTS 6,783,958 B2 * 8/2004 Nakai ..................... 435/69.1
2005/0273867 A1* 12/2005 Brulet et al. ................. 800/8

OTHER PUBLICATIONS

Berridge et al., (2003) Calcium Signalling: Dynamics, Homeostasis and Remodelling, *Nature Rev. Mol. Cell. Biol.* 4, 517-29.
Lewis et al., (2001) Calcium Signalling Mechanisms in T Lymphocytes, *Annu. Rev. Immunol.* 19, 497-521.
Missiaen et al., (1994) Kinetics of Empty Store-ctivated $Ca^{2+}$ Influx in HeLa Cells, *J. Biol. Chem.* 269, 5817-23.
Montero et al., (2001) Stimulation by Thimerosal of Histamine-Induced $Ca^{2+}$ Release in intact HeLa Cells Seen with Aequorin Targeted to the Endoplasmic Reticulum, *Cell Calcium* 30, 181-90.
Mikoshiba et al., (2000) $IP_3$ Receptor-Operated Calcium Entry, *Sci. STKE* 2000, PE1.
Putney et al., (1986) A Model for Receptor-Regulated Calcium Entry, *Cell Calcium* 7, 1-12.
Putney et al., (2001) Mechanisms of Capacitative Calcium Entry, *J. Cell Sci.* 114, 2223-29.
Prakriya et al., (2003) CRAC Channels:Activation, Permeation, and the Search for a Molecular Identity, *Cell Calcium* 33, 311-21.
Roos et al., (2005) STIM1, An Essential and Conserved Component of Store-Operated $Ca^{2+}$ Channel Function, *J Cell Biol.*, 169, 435-45.
Williams et al., (2002) Stromal Interaction Molecule 1 (STIM1), a Transmembrane Protein with Growth Suppressor Activity, Contains an Extracellular SAM Domain Modified by *N*-linked Glycosylation, *Biochim Biophys Acta.* Apr. 1;1596(1):131-7.
Williams et al. (2001) Identification and Characterization of the STIM (Stromal Interaction Molecule) Gene Family: Coding for A Novel Class of Transmembrane Proteins, *Biochem J.* Aug. 1;357(Pt 3):673-85.

* cited by examiner

*Primary Examiner*—Maryam Monshipouri
*Assistant Examiner*—Marsha M Tsay
(74) *Attorney, Agent, or Firm*—Carol L. Francis; David A. Carpenter; Bozicevic, Field & Francis LLP

(57) ABSTRACT

The invention features methods and compositions for determining states of intracellular calcium stores in a eukaryotic cell. Also provided are methods for identifying an agent (e.g., a gene product or small molecule compound) that modulates intracellular calcium store levels (e.g., by modulating store operated calcium (SOC) influx), as well as kits and systems for practicing the subject methods.

11 Claims, 13 Drawing Sheets
(4 of 13 Drawing Sheet(s) Filed in Color)

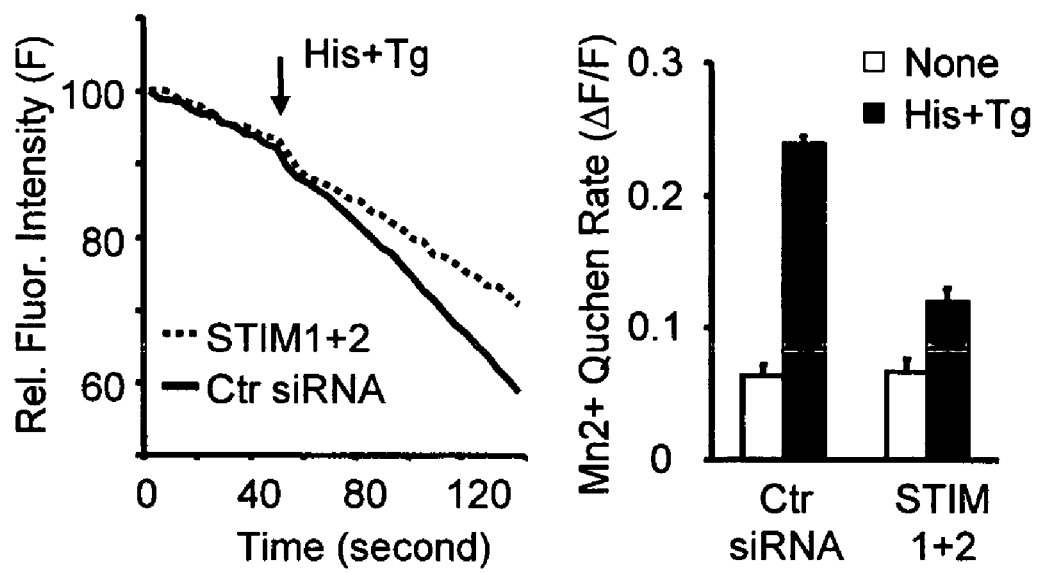
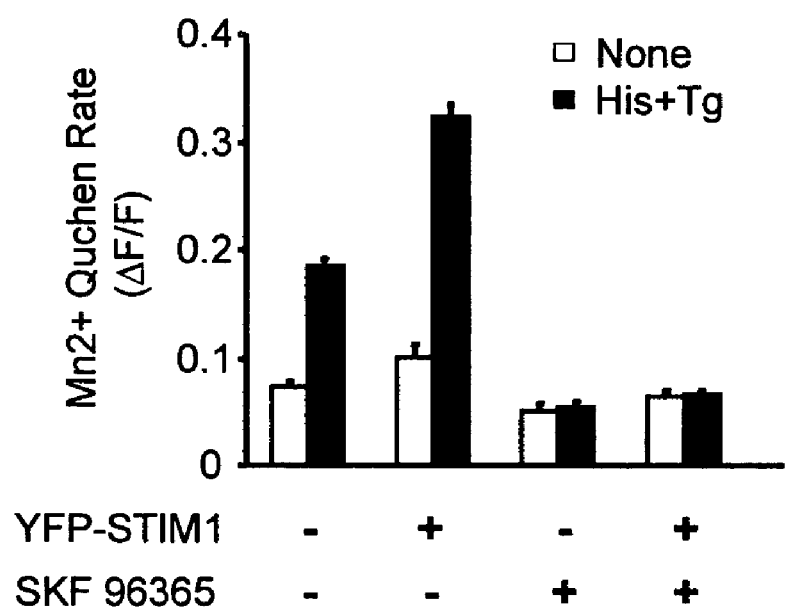
FIG. 2

Amino Acid Sequence of "SP-YFP-STIM1"

signal peptide, aa 1-22 of the original STIM1 cDNA { MDVCVRLALWLLWGLLLHQGQS

*Italic: (linker sequence)* { *LAPVAT*

Enhanced YFP {
MVSKGEELFTGVVPILVELDGDVNGHKFSVSGEGEGDATYGKLTLKFICTTGKLP
VPWPTLVTTFGYGLQCFARYPDHMKQHDFFKSAMPEGYVQERTIFFKDDGYKA
EVKFEGDTLVNRIELKGIDFKEDGNILGHKLEYNYNSHNVYIMADKQKNGIKVN
FKIRHNIEDGSVQLADHYQQNTPIGDGPVLLPDNHYLSYQSALSKDPNEKRDHM
VLLEFVTAAGITLGMDELYK

*Italic: (linker sequence)* { *SGSTSLYKKAGS*

LSHSHSEKATGTSSGANSEESTAAEFCRIDKPLCHSEDEKLSFE

EF hand {
AVRNIHKLMDDDANGDVDVEESDEFLRED
LNYHDPTVKHSTFHGEDKLISVEDLWKAWKSSEVY

SAM domain {
NWTVDEVVQWLITYVELPQYEETFRKLQLSGHAMPRLAVTNTTMTGTVLKMTD
RSHRQKLQLKALDTVL
FGPPLLTRHNHLKD Transmembrane {
FMLVVSIVIGVGGCWFAYI
QNRYSKEHMKKMMKDLEGLH ERM domain {
RAEQSLHDLQERLHKAQEEHRTVEVEKVHLEKKLRDEINLAKQEAQRLKELREG
TENERSRQKYAEEELEQVREALRKAEBKELESHSSWYAPEALQKWLQLTHEVEV
QYYNIKKQNAEKQLLVAKEGAEKIKKKRNTLFGTFHVAHSSSLDDVDHKILTAK
QALSEVTAALR ERLHRWQQEILCGFQIVNNPGIHSLVAALNIDPSWMGSTRPNPAHFIMTDDVDD
MDEEIVSPLSMQSPSLQSSVRQRLTEPQHGLGSQRDLTHSDSESSLHMSDRQRVA
PKPPQMSRAADEALNAMTSNGSHRLIEGVHPGSLVEKLPDSPALAKKALLALNH
GLDKAHSLMELSPSAPPGGSPHLDSSRSHSPSSPDPDTPSPVGDSRALQASRNTRIP
HLAGKKAVAEEDNGSIGEETDSSPGRKKFPLKIFKKPLKK

FIG. 9A

Coding sequence for SP-YFP-STIM1 atggatgtatgcgtccgtcttgccctgtggctcctctggggactcctcctgcaccagggccagagcctcgcaccggtcgccacc
atggtgagcaagggcgaggagctgttcaccggggtggtgcccatcctggtcgagctggacggcgacgtaaacggccacaag
ttcagcgtgtccggcgagggcgagggcgatgccacctacggcaagctgaccctgaagttcatctgcaccaccggcaagctgc
ccgtgccctggcccaccctcgtgaccaccttcggctacggcctgcagtgcttcgcccgctaccccgaccacatgaagcagcac
gacttcttcaagtccgccatgcccgaaggctacgtccaggagcgcaccatcttcttcaaggacgacggcaactacaagacccg
cgccgaggtgaagttcgagggcgacaccctggtgaaccgcatcgagctgaagggcatcgacttcaaggaggacggcaacat
cctggggcacaagctggagtacaactacaacagccacaacgtctatatcatggccgacaagcagaagaacggcatcaaggtg
aacttcaagatccgccacaacatcgaggacggcagcgtgcagctcgccgaccactaccagcagaacacccccatcggcgac
ggccccgtgctgctgcccgacaaccactacctgagctaccagtccgccctgagcaaagaccccaacgagaagcgcgatcaca
tggtcctgctggagttcgtgaccgccgcgggatcactctcggcatggacgagctgtacaagtccggatcaacaagtttgtacaa
aaaagcaggctccctcagccatagtcacagtgagaaggcgacaggaaccagctcggggggccaactctgaggagtccactgc
agcagagttttgccgaattgacaagcccctgtgtcacagtgaggatgagaaactcagcttcgaggcagtccgtaacatccacaa
actgatggacgatgatgccaatggtgatgtggatgtggaagaaagtgatgagttcctgagggaagacctcaattaccatgaccc
aacagtgaaacacagcaccttccatggtgaggataagctcatcagcgtggaggacctgtggaaggcatggaagtcatcagaag
tatacaattggaccgtggatgaggtggtacagtggctgatcacatatgtggagctgcctcagtatgaggagaccttccggaagct
gcagctcagtggccatgccatgccaaggctggctgtcaccaacaccaccatgacagggactgtgctgaagatgacagaccgg
agtcatcggcagaagctgcagctgaaggctctggatacagtgctctttgggcctcctctcttgactcgccataatcacctcaagga
cttcatgctggtggtgtctatcgttattggtgtgggcggctgctggtttgcctatatccagaaccgttactccaaggagcacatgaa
gaagatgatgaaggacttggagggggttacaccgagctgagcagagtctgcatgaccttcaggaaaggctgcacaaggcccag
gaggagcaccgcacagtggaggtggagaaggtccatctggaaaagaagctgcgcgatgagatcaaccttgctaagcaggaa
gcccagcggctgaaggagctgcggaagggtactgagaatgagcggagccgccaaaaatatgctgaggaggagttggagca
ggttcgggaggccttgaggaaagcagagaaggagctagaatctcacagctcatggtatgctccagaggcccttcagaagtggc
tgcagctgacacatgaggtggaggtgcaatattacaacatcaagaagcaaaatgctgagaagcagctgctggtggccaaggag
ggggctgagaagataaaaagaagagaaacacactctttggccacttccacgtggcccacagctcttccctggatgatgtagat
cataaaattctaacagctaagcaagcactgagcgaggtgacagcagcattgcgggagcgcctgcaccgctggcaacagatcg
agatcctctgtggcttccagattgtcaacaaccctggcatccactcactggtggctgccctcaacatagaccccagctggatggg
cagtacacgccccaaccctgctcacttcatcatgactgacgacgtggatgacatggatgaggagattgtgtctcccttgtccatgc
agtcccctagcctgcagagcagtgttcggcagcgcctgacggagccacagcatggcctgggatctcagagggatttgacccat
tccgattcggagtcctccctccacatgagtgaccgccagcgtgtggccccaaacctcctcagatgagccgtgctgcagacga
ggctctcaatgccatgacttccaatggcagccaccggctgatcgagggggtccacccagggtctctggtggagaaactgcctg
acagccctgccctggccaagaaggcattactggcgctgaaccatgggctggacaaggcccacagcctgatggagctgagccc
ctcagccccacctggtggctctccacatttggattcttcccgttctcacagcccagctccccagacccagacacaccatctccag
ttggggacagccgagccctgcaagccagccgaaacacacgcattccccacctggctggcaagaaggctgtggctgaggagg
ataatggctctattggcgaggaaacagactccagcccaggccggaagaagtttcctctcaaaatctttaagaagcctcttaagaa
gtag

FIG. 9B

```
            |-Signal Peptide-----|
STIM1:  MDVCVRLALWLLWGLLLHQGQSLSHSHSE----------------------------- 29

STIM2:  MNAAGIRAPEAAGADGTRLAPGGSPCLRRRGRPEESPAAVVAPRGAGELQAAGAPLRFHP 60

STIM1:  ------------------------------------------------------------

STIM2:  ASPRRLHPASTPGPAWGWLLRRRRWAALLVLGLLVAGAADGCELVPRHLRGR 112

|---EF Hand Domain-->
STIM1:  KATGTSSGANSEESTAA--------EFCRIDKPLCHSEDEKLSFEAVRNIHKLMDDDDANG 81
        +ATG+++ A S  + AA        + C    P C +E+++ S EA++ IHK MDDD +G
STIM2:  RATGSAATAASSPAAAAGDSPALMTDPCMSLSPPCFTEEDRFSLEALQTIHKQMDDDKDG 172

-------------|                              |---SAM Domain-->
STIM1:  DVDVEESDEFLREDLNYHDPTVKHSTFHGEDKLISVEDLWKAWKSSEVYNWTVDEVVQWL 141
         ++VEESDEF+RED+ Y D T KHS  H EDK I++EDLWK WK+SEV+NWT+++ +QWL
STIM2:  GIEVEESDEFIREDMKYKDATNKHSHLHREDKHITIEDLWKRWKTSEVHNWTLEDTLQWL 232

--------------------------------------------------------|
STIM1:  ITYVELPQYEETFRKLQLSGHAMPRLAVTNTTMTGTVLKMTDRSHRQKLQLKALDTVLFG 201
        I +VELPQYE+  FR   + G +PR+AV  +   + LK++DRSHRQKLQLKALD VLFG
STIM2:  IEFVELPQYEKNFRDNNVKGTTLPRIAVHEPSFMISQLKISDRSHRQKLQLKALDVVLFG 292

|--TM Domain------|             |----ERM Domain-->
STIM1:  PPLLTRHNHLKDFMLVVSIVIGVGGCWFAYIQNRYSKEHMKKMMKDLEGLHRAEQSLHDL 261
        P     HN +KDF+L VSIVIGVGGCWFAY QN+ SKEH+ KMMKDLE L  AEQSL DL
STIM2:  PLTRPPHNWMKDFILTVSIVIGVGGCWFAYTQNKTSKEHVAKMMKDLESLQTAEQSLMDL 352

---------------------(ERM Domain, cont.)-----------------
STIM1:  QERLHKAQEEHRTVEVEKVHLEKKLRDEINLAKQEAQRLKELREGTENERSRQKYAEEEL 321
        QERL KAQEE+R V VEK +LE+K+ DEIN AK+EA RL+ELREG E E SR++YAE+EL
STIM2:  QERLEKAQEENRNVAVEKQNLERKMMDEINYAKEEACRLRELREGAECELSRRQYAEQEL 412

---------------------(ERM Domain, cont.)-----------------
STIM1:  EQVREALRKAEKELESHSSWYAPEALQKWLQLTHEVEVQYYNIKKQNAEKQLLVAKEGAE 381
        EQVR AL+KAEKE E  SSW  P+ALQKWLQLTHEVEVQYYNIK+QNAE QL +AK+ AE
STIM2:  EQVRMALKKAEKEFELRSSWSVPDALQKWLQLTHEVEVQYYNIKRQNAEMQLAIAKDEAE 472

------------------(ERM Domain, cont.)----|
STIM1:  KIKKKRNTLFGTFHVAHSSSLDDVDHKILTAKQALSEVTAALRERLHRWQQIEILCGFQI 441
        KIKKKR+T+FGT HVAHSSSLD+VDHKIL AK+ALSE+T   LRERL RWQQIE +CGFQI
STIM2:  KIKKKRSTVFGTLHVAHSSSLDEVDHKILEAKKALSELTTCLRERLFRWQQIEKICGFQI 532

STIM1:  VNNPGIHSLVAALNIDPSWMGSTRPNPAHFIMTDDVDDMEE 483
        +N G+ SL ++L  D SW+   R +   + +    VDD+DE+
STIM2:  AHNSGLPSLTSSLYSDHSWVVMPRVSIPPYPIAGGVDDLDED 574

STIM1:  IVSPLSMQSPSLQSSVRQRLTEPQHGLGSQRDLTHSDSESSLHMSDRQRVAPKPPQM 540

STIM2:  TPPIVSQFPGTMAKPPGSLARSSSLCRSRRSIVPSSPQPQRAQLAPHAPHPSHPRHP 631
```

FIG. 10A

```
STIM1: SRAADEALNAMTSNGSHRLIEGVHPGSLVEKLPDSPALAKKALLALNHGLDKAHSLMELS 600

STIM2: HHPQHTPHSLPSPDPDILSVSSCPALYRNEEEEEAIYFSAEKQWEVPDTASECDSLNSSI 691

STIM1: PSAPPGGSPHLDSSRSHSPSSPDPDTPSPVGDSRALQASRNTRIPHLAGKKAVAEEDNGS 660

STIM2: GRKQSPPLSLEIYQTLSPRKISRDEVSLEDSSRGDSPVTVDVSWGSPDCVGLTETKSMIF 751

SITM1: IGEETDSSPGRKKFPLKIFKKPLKK-------------------------------- 685

STIM2: SPASKVYNGILEKSCSMNQLSSGIPVPKPRHTSCSSAGNDSKPVQEAPSVARISSIPHDL 811

STIM1: ---------------------

STIM2: CHNGEKSKKPSKIKSLFKKKSK 833
```

FIG. 10B

Signal Peptide (SP) encoding DNA inserted between NheI and AgeI site.
EYFP – Enhanced Yellow Fluorescent Protein
STIM w/o SP – STIM protein lacking signal peptide

CALCIUM BIOSENSOR POLYPEPTIDES AND METHODS OF USE

CROSS-REFERENCE TO PRIOR APPLICATIONS

This application claims priority benefit of U.S. provisional application Ser. No. 60/688,625, filed Jun. 7, 2005 and claims priority benefit of U.S. provisional application Ser. No. 60/688,807, filed Jun. 8, 2005, each of which is incorporated herein by reference in its entirety.

GOVERNMENT RIGHTS

This invention was made with government support under federal grant nos. R33CA083229, RO1GM063702, and RO1GM030179 awarded by National Institutes of Health. The United States Government may have certain rights in this invention.

BACKGROUND OF THE INVENTION

In virtually all cells, changes in cytoplasmic calcium ($Ca^{2+}$) concentration regulate cell functioning and signaling. Generally, a stimulus generates messenger signals that cause a release of calcium from sequestered intracellular stores (primarily found in the endoplasmic reticulum (ER)) and into the cytoplasm. The release of calcium from a sequestered intracellular store triggers calcium channels on the plasma membrane to open, which then leads to influx of calcium from the extracellular space into the cytoplasm and, in turn, into the store. The series of events between the initial release of stored calcium to the subsequent influx of calcium from the extracellular space into the cytoplasm is referred to as store-operated calcium influx (SOC influx). Sustained levels of increased cytoplasmic calcium are required for a number of physiologic responses, such as T-cell activation and differentiation.

The mechanisms that lead to calcium mobilization under physiological conditions have been studied. Stimulation of cells with a variety of physiological stimuli leads to an inositol-1,4,5-trisphosphate (InsP3)-mediated release of $Ca^{2+}$ from intracellular stores which in turn triggers an influx of $Ca^{2+}$ across the plasma membrane (Berridge et al., (2003) Nature Rev. Mol. Cell. Biol. 4, 517-29; Putney et al., (1986) Cell Calcium 7, 1-12; Mikoshiba et al., (2000) Sci. STKE 2000, PE1; Putney et al., (2001) J. Cell Sci. 114, 2223-29; Prakriya et al., (2003) Cell Calcium 33, 311-21; Lewis et al., (2001) Annu. Rev. Immunol. 19, 497-521; Missiaen et al., (1994) J. Biol. Chem. 269, 5817-23; Montero et al., (2001) Cell Calcium 30, 181-90).

Many of the signaling pathways leading from cell stimulation to the depletion of sequestered stores of calcium have been defined. However, the details of the subsequent pathway leading from $Ca^{2+}$ store depletion to $Ca^{2+}$ influx through the plasma membrane (also termed store operated $Ca^{2+}$ (SOC) influx or capacitative $Ca^{2+}$ entry pathway (Putney et al., (1986) Cell Calcium 7, 1-12; Mikoshiba et al., (2000) Sci. STKE 2000, PE1; Putney et al., (2001) J. Cell Sci. 114, 2223-29; Prakriya et al., (2003) Cell Calcium 33, 311-21)) have remained elusive. Recently, stromal interaction molecule (STIM)-1 (Williams et al., Biochim Biophys Acta. Apr. 1, 2002; 1596(1):131-7; Williams et al. Biochem J. Aug. 1, 2001; 357(Pt 3):673-85) was reported to play a role in the signaling processes that comprise SOC influx. (Roos et al., (2005) J Cell Biol., 169, 435-45) However, an understanding of the mechanisms through which STIM1 facilitates the calcium-based signaling processes has not been reported.

A few conventional methods are available for assessing calcium influx. These include patch clamp studies, which detect changes in calcium concentrations through detection of changes in current across a membrane. Patch clamp studies, however, are not readily adapted to high throughput assays. Other calcium influx assays involve loading cells with a dye, such as FLUO-3™, and FLUO-4™, and FURA-2™, which is sensitive to intracellular concentrations of calcium. However, these assays require the cells to be "loaded" with dye prior to, for example, evaluating the effects of an agent upon calcium signaling. Also, the dye can leak from the cells, decreasing the sensitivity of the assay as well the period of time over which an assay can be conducted. The dye can also affect calcium buffering in the cell, thus affecting the reliability and accuracy of the results. The dye can also be toxic for cells, again affecting the ability to accurately assay effects upon calcium signaling.

Accordingly, there remains a need in this art for methods to monitor changes in modulation of calcium levels in a cell and calcium signaling. The present invention addresses this need.

SUMMARY OF THE INVENTION

The invention features methods and compositions for determining a state of intracellular calcium stores in a eukaryotic cell. Also provided are methods for identifying an agent (e.g., a gene product or small molecule compound) that modulates intracellular calcium levels (e.g., by modulating store operated calcium (SOC) influx), as well as kits and systems for practicing the subject methods.

In one aspect the invention features a method of assessing calcium levels in a cell, the method comprising detecting a calcium biosensor polypeptide (CBP) distribution pattern in a cell comprising a CBP, wherein the CBP comprises a detectable domain, wherein the CBP distribution pattern is indicative of intracellular calcium store levels in the cell. In a related embodiment, the detectable domain is a fluorescent polypeptide. In another related embodiment, a punctate CBP distribution pattern is indicative of depletion of intracellular store calcium. In another related embodiment a diffuse CBP distribution pattern is indicative of levels intracellular store calcium that are not depleted.

In another aspect the invention features a method of monitoring store-operated $Ca2^+$ influx in a cell, the method comprising detecting a calcium biosensor polypeptide (CBP) distribution pattern in a cell comprising a CBP, wherein the CBP comprises a detectable domain, wherein the CBP distribution pattern is indicative of a state of SOC influx. In a related embodiment, the detectable domain is a fluorescent polypeptide. In further related embodiment, a punctate CBP distribution pattern indicates the cell is undergoing or is about to undergo SOC influx.

In another aspect the invention features a method of screening a candidate agent comprising detecting a calcium biosensor polypeptide (CBP) distribution pattern in a cell comprising a CBP, wherein the CBP comprises a detectable domain, and wherein the CBP distribution pattern in the presence of the candidate agent indicates the candidate agent modulates intracellular calcium store levels in the cell. In a related embodiment, the cells are cultured in the presence of an agonist or antagonist of a calcium signaling pathway. In another related embodiment, a lack of a significant punctate CBP distribution pattern indicates the candidate agent has no detectable effect upon intracellular store calcium levels in the cell. In another related embodiment, a formation of a punctate CBP distribution pattern indicates the candidate agent facilitates depletion of an intracellular calcium store.

In another aspect the invention features a calcium biosensor polypeptide (CBP) comprising a STIM polypeptide comprising a heterologous detectable domain positioned N-terminal to an EF hand domain of the STIM polypeptide. In a related embodiment, the CBP further comprises a signal polypeptide positioned N-terminal to the detectable domain. In further related embodiment, the heterologous detectable domain is a fluorescent polypeptide.

In another aspect the invention features a polynucleotide encoding a CBP of the invention. In a related embodiment, the invention provides a host cell comprising a polynucleotide of the invention. In a further related embodiment, the invention provides an array comprising the host cell of the invention.

In another aspect the invention features a calcium-insensitive marker (CIM) polypeptide comprising a STIM polypeptide comprising a heterologous detectable domain positioned N-terminal to a mutant EF hand domain, wherein the mutant EF hand domain is modified to have decreased calcium binding affinity relative to a wild-type EF hand domain. In a related embodiment, the CIM polypeptide further comprises a signal polypeptide positioned N-terminal to the detectable domain. In a related embodiment, the heterologous detectable domain is a fluorescent polypeptide. In related embodiments, the invention provides for a polynucleotide encoding the CIM polypeptide of the invention. In further related embodiments, the invention provides for a host cell comprising the polynucleotide encoding the CIM polypeptide of the invention. In further related embodiments, the host cell further comprises the polynucleotide encoding a CBP of the invention.

In further related embodiments, the invention provides for an array comprising the host cell comprising the polynucleotide encoding the CIM polypeptide of the invention and the polynucleotide encoding a CBP of the invention.

In another aspect the invention features a kit comprising the host cell comprising a polynucleotide encoding a CBP of the invention and instructions for use. In a related embodiment, the kit further comprises the host cell comprising a polynucleotide encoding a CIM polypeptide of the invention.

The invention is advantageous in many respects. For example, the invention provides the advantage that assays can be conducted using a stably modified cell that can provide for stable expression of a calcium biosensor polypeptide (CBP) and/or calcium-insensitive marker polypeptide (CIM) of the invention. Thus, the invention avoids many of the disadvantages of the assays that use dyes as discussed above, e.g., there is no requirement for loading of cells prior to assays, the detectable signal associated with the biosensors and markers of the invention do not leak from the cells, cell toxicity associated with dyes is avoided, etc.

The invention is also advantageous in that it can be used to assess the level of calcium in the intracellular store. In contrast, dye-based assays and other conventional assays usually only measure the overall intracellular calcium levels in the cell. Measuring calcium in stores using conventional dye-based assays requires extensive manipulation of the cell. The present invention allows one to assess, in a single assay and without the need for additional manipulation of cells, the effect of an agent or other stimulus upon SOC influx.

Another advantage of the invention is that assays can be conducted to assess, for example, effect of agents or other stimuli upon depletion of intracellular calcium stores and/or restoration of intracellular calcium stores. The CBPs of the invention exploit STIM polypeptides, which respond to a step in the calcium mobilization pathway that is upstream of SOC influx. Thus, the assays of the invention for the first time provide a means to distinguish the effects of an agent or other stimulus upon depletion of calcium stores, modulation of SOC influx, and replenishment of calcium stores. The invention thus allows one to determine what part of the calcium mobilization pathway the agent or other stimulus affects.

Another advantage of the invention is that assays can be conducted so that reversible effects of a candidate agent or other environmental stimulus can be examined.

Still another advantage of the invention is that the CBP distribution patterns are maintained upon fixing the cells. Thus, for example, the assays can be conducted by exposing the cells to an agent or other stimulus, and fixing the cells at different time points after exposure. The fixed cells can then be examined for the effects of the agent at a later time. This feature makes the assays readily amenable to high throughput assays, and allows for examination of many samples without the time constraints of assays that require examining the effects of the agent in live cells.

These and other advantages, aspects, features, and embodiments will be readily apparent to the ordinarily skilled artisan upon reading the present specification.

BRIEF DESCRIPTION OF THE DRAWINGS

The patent or application file contains at least one drawing executed in color. Copies of this patent or application publication with color drawing(s) will be provided by the U.S. Patent and Trademark Office upon request and payment of necessary fee.

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2 is a set of graphs showing that STIM regulates SOC influx. Panel A: Direct measurement of Ca$^{2+}$ influx using a Mn$^{2+}$ quench assay. HeLa cells were transfected for 2 days with 20 nM control or a mix of 10 nM STIM1 and 10 nM STIM2 siRNAs. 2 mM Mn$^{2+}$ was added before image acquisition and 100 μM histamine plus 2 μM thapsigargin were added 50 seconds after. The left panel shows the relative Fura-2 fluorescence intensity measured using 360 nm excitation as a function of time in control and STIM knockdown cells. Each trace represents the average quench response of three separate experiments, with 660 to 1,300 individual cells analyzed per experiment. A Matlab program was used to calculate the ΔF/F quench rate in each cell before (4 to 44 s) and after (100 to 140 s) stimulus addition. The average ΔF/F is shown in a bar graph on the right. Panel B: Overexpression of YFP-STIM1 enhances SOC influx. HeLa cells transfected with 40 ng of YFP-STIM1 or control vector for 1 day were subjected to Mn$^{2+}$ quench assays as described in Panel A. A SOC influx inhibitor, SKF 96365, was used at 20 μM. Over 150 individual cells were analyzed for each data set. Error bars are 95% confidence bounds.

FIGS. 9A and 9B are schematics showing the amino acid sequence (SEQ ID NO:02) (FIG. 9A) and DNA sequence (SEQ ID NO:01) (FIG. 9B) of an exemplary calcium biosensor polypeptide, which has a backbone amino acid sequence of human STIM1 and enhanced YFP as a detectable domain (SP-YFP-STIM1).

FIGS. 10A-10B are schematics showing an alignment of the amino acid sequences of human STIM1 (SEQ ID NO:03) and human STIM2 (SEQ ID NO:04) (precursors), with SEQ ID NO:05 indicating the shared amino acid residues.

DEFINITIONS

Figure 1:
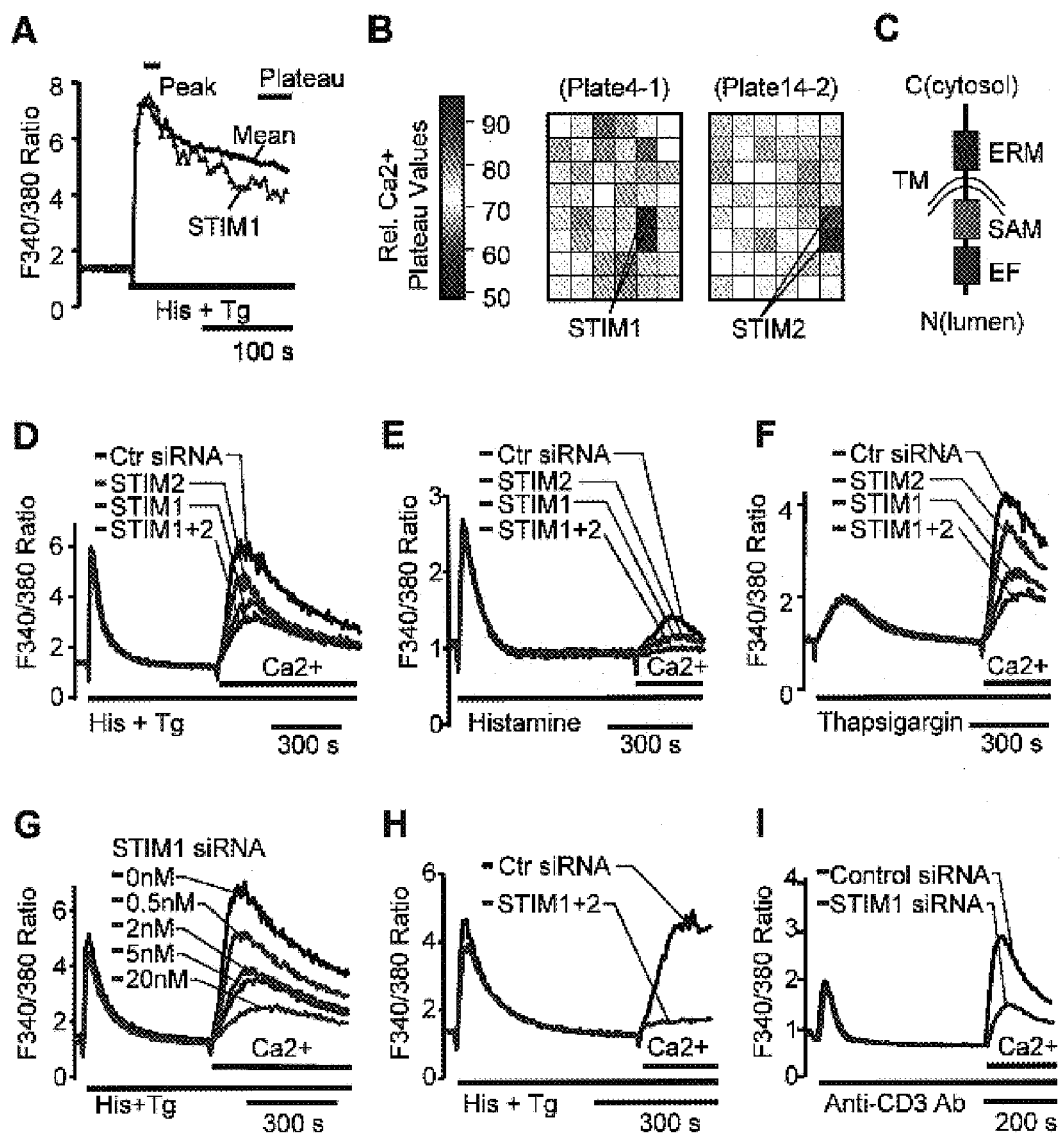
FIG. 1 is a series of graphs and a schematic relating to the identification of STIM1 and STIM2 in a kinetic $Ca^{2+}$ screen for suppression of SOC influx. Panel A: A graph showing a comparison of the $Ca^{2+}$ time-course in STIM1 knockdown cells to the averaged reference time-course. HeLa cells were transfected with the siRNA signaling set at an average concentration of 10 nM for 2 days. Fura-2 $Ca^{2+}$ time-courses were measured in a microplate reader using automated stimulus addition. Panel B: A graph depicting positional heat map analysis of relative $Ca^{2+}$ plateau values in the two microplates containing STIM1 and STIM2 siRNA-transfected cells (24 duplicate siRNAs per plate). Relative $Ca^{2+}$ plateau values were calculated by dividing the plateau (the average of the last 5 data points) by the peak (the average of 3 peak points) fluorescence. Panel C: A schematic showing domain structure of STIM1 and STIM2. Domains include an EF-hand motif (EF), a sterile alpha motif (SAM) domain, a single transmembrane domain (TM), and an ERM domain arranged from N to C terminus of both proteins with the C-terminus in the cytosol. Panels D-F: Is a set of graphs showing suppression of $Ca^{2+}$ influx by STIM siRNAs measured by "$Ca^{2+}$ add-back" in HeLa cells transfected with 10 nM STIM1 and/or 10 nM STIM2 siRNA for 2 days. 100 µM histamine plus 2 µM thapsigargin (Panel D), or histamine alone (Panel E), or thapsigargin alone (Panel F) were used to deplete $Ca^{2+}$ stores. Panel G: A graph showing titration of STIM1 siRNA. Total siRNA concentration was kept at 20 nM for all samples using control siRNA. Panel H: A graph showing near complete inhibition of $Ca^{2+}$ influx in cells transfected for 3 days with 20 nM STIM1 plus 20 mM STIM2 siRNA. Panels D-H: Graphs showing data that are the average of 3 bulk-cell $Ca^{2+}$ measurements obtained using a microplate reader. Panel I: A graph showing suppression of T-cell receptor-triggered $Ca^{2+}$ influx by STIM1 siRNA. Ca$^{2+}$ add-back experiments were done in Jurkat T cells transfected with pYFP-Nuc (transfection marker) plus 72 nM STIM1 or control siRNA for 2 days. Ca$^{2+}$ stores were depleted using 20 μg/ml anti-human CD3 antibody. Shown are the average Ca$^{2+}$ responses of 48 control and 84 STIM1 siRNA transfected (YFP-positive) single cells.

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

As used herein "calcium biosensor polypeptide" or "CBP" refers to a detectably labeled calcium-binding polypeptide that 1) forms a punctuate pattern associated with membranes of an organelle storing calcium (e.g., the endoplasmic reticulum (ER)) when calcium is not bound to the polypeptide, indicating relative depletion of stored calcium, and 2) forms a diffuse or non-punctate pattern in a membrane of a calcium-storing organelle (e.g., the ER) when calcium is not depleted. As a result, distinctly detectable patterns associated with the calcium biosensor state are generated in response to a state of intracellular calcium store levels.

"Calcium insensitive marker" or "CIM" as used herein generally refers to a polypeptide having the properties of a CBP, but having a modified EF hand domain that results in reduced binding affinity for calcium relative to, for example, an EF hand domain of a CBP. As a result, a CIM provides a punctate pattern irrespective of the state of intracellular calcium stores in a cell.

A "distribution pattern" refers to a pattern of CBP distribution or CIM distribution on a membrane of a cell, usually on an endoplasmic reticulum membrane, which is provided by a detectable signal associated with a detectable domain of the CBP or CIM. The distribution pattern of a CBP can be a diffuse pattern when a cell is in a state of normal intracellular calcium (i.e., when intracellular calcium stores are normal, also referred to herein as an intracellular calcium replete state) and present in a punctate pattern when a cell is in an intracellular calcium store depleted state. CIMs provide a punctate pattern regardless of the intracellular calcium state of the cell.

As used herein "calcium biosensor state" refers to the distribution of a calcium biosensor polypeptide within a cell (e.g., the presence of the biosensor in an aggregate of biosensor polypeptides so as to provide a punctate pattern, or as more discrete polypeptides to provide a diffuse pattern), which state depends on the calcium binding state of the biosensor polypeptide (e.g., presence or absence of bound calcium).

As used herein, "cell's physiologic state with respect to SOC influx" and "cell's state of SOC influx" refers to the intracellular calcium state of a cell with respect to influx of calcium in response to depleted intracellular calcium stores.

Unless indicated otherwise either specifically or by context, "intracellular calcium" generally refers to "cytosolic calcium" in a cell; "intracellular store calcium", "store calcium", "stored intracellular calcium", or "intracellular calcium stores", and the like, refers to calcium in sequestered in the ER or other organelles in a cell.

"Low level of intracellular store calcium" in a cell as used herein refers to a calcium state in the store that is depleted relative to normal, and generally refers to a state in the cell in which a STIM polypeptide would form puncta in a cell membrane, e.g., in the endoplasmic reticulum membrane. In general "normal intracellular store calcium" refers to a state of the cell in which the concentration of calcium in intracellular stores is about 50 µM to about 400 µM. In general, under physiological conditions, normal cytosolic calcium concentrations are about 100 nM, and normal extracellular calcium concentrations are generally about 1 mM.

The term "modulates", as in, for example, "modulates calcium levels", "modulates calcium mobilization", or "modulates intracellular calcium store levels", particularly in reference to an agent (e.g., a candidate agent) is meant that the agent directly or indirectly effects an increase or decrease in the associated cellular event.

The term "stimulus" refers to an environmental condition, e.g., exposure to an agent, temperature, light, osmolarity, and the like, which may elicit a response, e.g., modulation of calcium signaling which can be associated with a change in intracellular store calcium levels, SOC influx, and the like.

The term "agent" includes any substance, molecule, element, compound, entity, or a combination thereof. It includes, but is not limited to, e.g., proteins (including antibodies), oligopeptides, small organic molecules, polysaccharides, polynucleotides (e.g., DNA or RNA, including polynucleotides encoding a gene product of interest, or which act as a cell modulator without transcription or without translation), and the like. It can be a natural product, a synthetic compound, or a chemical compound, or a combination of two or more substances. Unless otherwise specified, the terms "agent," "substance," and "compound" can be used interchangeably.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

The term "biological preparation" refers to biological samples taken in vivo or in vitro (either with or without subsequent manipulation), as well as those prepared synthetically. Representative examples of biological preparations include cells, tissues, solutions and bodily fluids, lysates of natural or recombinant cells, and samples derived from such sources.

As used herein, the term "functional derivative" of a native protein or a polypeptide is used to define biologically active amino acid sequence variants that possess the biological activities (either functional or structural) that are substantially similar to those of the reference protein or polypeptide.

The terms "substantially pure" or "isolated," when referring to proteins and polypeptides denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Sequence identity" refers to a number of residues shared between a query amino acid sequence and a reference amino acid sequence (or between a query nucleotide sequence and a reference nucleotide sequence) over a region of alignment. In general, sequence identity is calculated based on a reference sequence, which may be a subset of a larger sequence, such as a conserved motif, coding region, flanking region, etc. A reference sequence will usually be at least about 6 amino acids long, usually at least about 10 amino acids long (or about 18 nt long, more usually at least about 30 nt long), and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment. Thus, where 98 residues of a 100 residue query sequence matches a test sequence, the percent identity would be 98 divided by 100, or 98%. Algorithms for computer-based amino acid and nucleotide sequence analysis are known in the art, such as BLAST (see, e.g., Altschul et al., J. Mol. Biol., 215:403-10 (1990)), particularly the Smith-Waterman homology search algorithm as implemented in MPSRCH program (Oxford Molecular). For the purposes of this invention, a preferred method of calculating percent identity is the Smith-Waterman algorithm, using the following: Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "recombinant" when used with reference to a cell indicates that the cell replicates a heterologous nucleic acid, or expresses a peptide or protein encoded by such a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence", "heterologous nucleic acid", "heterologous polypeptide" or "heterologous amino acid sequence" as used herein, is one that originates from a source foreign to the particular host cell, or, if from the same source, is modified from its original form. Thus, a heterologous nucleic acid in a host cell includes nucleic acid that, although being endogenous to the particular host cell, has been modified (e.g., so that it encodes an amino acid sequence different from that of the endogenous nucleic acid, to a nucleic acid to provide a sequence not normally found in the host cell, and the like). Modification of the heterologous sequence can occur, e.g., by treating the DNA with a restriction enzyme to generate a DNA fragment that is capable of being operably linked to the promoter or by operably linking the DNA to a heterologous promoter to provide an expression cassette that is not endogenous to the host cell. Techniques such as site-directed mutagenesis are also useful for modifying a heterologous nucleic acid.

The term "operably linked" refers to functional linkage between nucleic acids to provide a desired activity, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., a nuclear localization signal is operably linked to a heterologous amino acid sequence to provide to association of the fusion protein with the nucleus in a mammalian cell).

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

As used herein, "contacting" has its normal meaning and refers to combining two or more entities (e.g., two proteins, a polynucleotide and a cell, a cell and a candidate agent, etc.). Contacting can occur in vitro (e.g., two or more agents [e.g., a test compound and a cell lysate] are combined in a test tube or other container) or in situ (e.g., two polypeptides can be contacted in a cell by coexpression in the cell, of recombinant polynucleotides encoding the two polypeptides), in a cell lysate.

By "genetic transformation" is meant a permanent or transient genetic change induced in a cell following incorporation of exogenous nucleic acid (e.g., DNA or RNA exogenous to the cell). Genetic change can be accomplished by, for example, incorporation of exogenous DNA into the genome of a host cell, by transient or stable maintenance of the exogenous DNA as an episomal element, or by transient introduction of an exogenous RNA into the host cell. Where the cell is a mammalian cell, a permanent genetic change is generally achieved by introduction of the DNA into the genome of the cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4+ cells, T lymphocytes, macrophages, peripheral blood mononuclear cells (PBMC), and the like. The term "biological sample" encompasses a clinical sample, and also includes cells in culture, cell supernatants, tissue samples, organs, bone marrow, and the like.

DETAILED DESCRIPTION OF THE INVENTION

Methods and compositions for assessing a cell's physiological state with respect to levels of stored intracellular calcium are provided. In general, the invention provides a calcium biosensor polypeptide (CBP) that provides a detectable (e.g., fluorescence) distribution pattern indicative of a calcium biosensor state, which in turn reflects a cell's physiological state, e.g., with respect to intracellular store calcium levels, SOC influx, and the like. In practicing the subject methods, levels of intracellular calcium stores are assessed in a cell having at least one CBP by analyzing a CBP fluorescence pattern. Also provided are methods for identifying an agent (e.g., a gene product or small molecule compound) that modulates intracellular stored calcium levels or a cell's state of SOC influx by detecting a change in a calcium biosensor state. The invention also provides kits and systems for practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the biosensor" includes reference to one or more biosensor and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Various biochemical and molecular biology methods referred to herein are well known in the art, and are described in, for example, Sambrook et al., Molecular Cloning: A Laboratory Manual, Cold Spring Harbor Press, N.Y. Second (1989) and Third (2000) Editions, and Current Protocols in Molecular Biology, (Ausubel, F. M. et al., eds.) John Wiley & Sons, Inc., New York (1987-1999).

OVERVIEW OF THE INVENTION

The present invention provides methods and compositions for monitoring both calcium biosensor polypeptide conformation and SOC influx of cells. Without being held to theory, the invention is based on the discovery that at least a part of the mechanism of action of STIM polypeptides, including both STIM1 and STIM2, involves distribution of STIM polypeptides in the membranes of endoplasmic reticulum (ER), an organelle which sequesters calcium. The inventors have discovered that when intracellular calcium stores are at normal levels, STIM polypeptides are distributed in a diffuse pattern over ER membranes. The inventors have further discovered that STIM polypeptides aggregate to form puncta in response to an actual or effective depletion of calcium from intracellular stores. In response to an actual or effective repletion of calcium, the puncta disassociate, again providing a more diffuse pattern of STIM polypeptides in the ER membrane. Thus, changes in the presence or absence of puncta (or the presence or absence of a diffuse pattern) are indicative of the distribution of STIM polypeptides in the cell, which in turn are indicative of the state of stored calcium levels in the cell. Thus changes in the pattern of STIM polypeptide distribution in the cell, e.g., in the ER membrane, are indicative of the cell's physiological state with respect to calcium, e.g., whether the cell is in a state of SOC influx or not.

The inventors have also discovered that modification of an EF hand domain of STIM polypeptides to decrease binding affinity for calcium results in maintenance of the protein in the punctate pattern associated with depleted calcium stores regardless of the level of calcium in the stores (e.g., regardless of whether the store of calcium is depleted or not).

The inventors have exploited these observations to provide a calcium biosensor polypeptide (CBP) of the invention, and methods of assessing a calcium state and/or SOC influx in a cell using such CBPs. Furthermore, the inventors have exploited the modified STIM polypeptide having a modified EF hand domain to provide a calcium-insensitive marker (CIM) which maintains a punctate pattern regardless of the calcium state of the cell (e.g., the punctate pattern is maintained even when intracellular stores of calcium are normal or replenished from a low level).

As provided in greater detail below, the subject methods of the present invention are practiced using a cell containing a calcium biosensor polypeptide that provides a detectable pattern (e.g., a fluorescent pattern) indicative of a calcium biosensor state, and thus a state with respect to calcium signaling, calcium store levels, and SOC influx. Assessing the detectable pattern in real time or at a given time point can be used to determine the calcium biosensor state. Accordingly the subject methods can be used for identifying an agent (e.g., a gene product or small molecule compound) that modulates the calcium biosensor state, and thus modulates calcium signaling, calcium store levels, and/or the cell's state of calcium influx.

The methods of the present invention are premised on the use of one or more genetically encoded calcium biosensor polypeptides that can be used to directly monitor the calcium biosensor state. In general, the calcium biosensor polypeptide described herein each contain a detectable domain, usually a fluorescent polypeptide, operably linked to a STIM polypeptide, usually at a position N-terminal to the EF hand domain of the STIM polypeptide. As a result, distinct detectable distribution patterns associated with the calcium biosensor state are generated.

For example, in one embodiment the calcium biosensor polypeptide contains a fluorescent polypeptide operably linked to the calcium responsive polypeptide STIM1. When the EF hand domain of STIM1 is bound by calcium present in the store, STIM1 remains dispersed throughout a cellular membrane, particularly the ER membrane. In this state, the protein provides as a granulated, dispersed pattern, generally referred to herein as a "diffuse" pattern. When STIM1 senses low calcium at its EF hand domain (e.g., due to decreased binding of the EF hand domain to calcium), STIM1 aggregates in membranes, providing a punctate pattern.

The methods of the subject invention are simple and rapid to perform. The methods provide a highly sensitive and specific assay, allowing determination of the calcium biosensor state and thus a cell's state of intracellular store calcium, SOC influx state, and the like. This assay not only offers a powerful tool to interpret calcium biosensor information, but can also be used to identify new modulators of calcium signaling, calcium binding to calcium biosensor polypeptides, mobilization of calcium from intracellular stores, mobilization of calcium to replenish stores (e.g., as a result of calcium mobilization into stores following SOC influx), where such modulators can range from small molecules, endogenous or non-endogenous gene products, and environmental stimuli.

The following description provides guidance for making and using the compositions of the invention, and for carrying out the methods of the invention.

Calcium Biosensor Polypeptides

In general, calcium biosensor polypeptides (CBPs) of the present invention include domains of a STIM polypeptide, and generally comprise, from N- to C-terminus: 1) a signal peptide (in the precursor form), 2) a detectable domain, e.g., a fluorescent polypeptide domain; and 3) an EF-hand domain, 4) a SAM domain, 5) a transmembrane domain, and 6) an ERM domain.

Without being held to theory, the presence or absence of calcium bound to the EF-hand domain of the CBP modulates changes in localization of the CBP in the cell. In particular, when calcium levels are low, and thus the EF-hand domain is not bound by calcium, CBP forms aggregates in cell membranes, e.g., in the ER plasma membrane. When calcium levels are relatively higher and calcium is bound to the EF hand domain, the CBP does not aggregate and thus is spread in a more diffuse pattern in cell membranes, e.g., in the ER plasma membrane Accordingly, following expression of the CBP, these changes in CBP conformation or distribution patterns can be detected by detecting changing patterns in the detectable signals (e.g., puncta formation or disappearance when fluorescent polypeptide domains are used), wherein the changes are indicative of the cell's physiological state with respect to SOC influx.

Structure of CBPs

The CBPs of the invention can be a naturally-occurring STIM polypeptide, or a STIM polypeptide modified to contain a detectable domain. In one embodiment, the CBP comprises an amino acid sequence of a STIM polypeptide (e.g., a STIM1 or STIM2 polypeptide) as a "backbone" of the CBP, with a heterologous detectable domain provided in the backbone, e.g., by insertion and/or replacement of amino acids in the STIM polypeptide sequence, usually at a position N-terminal to the EF hand domain (e.g., in the precursor, usually at a position between the signal peptide and the EF hand domain). In other embodiments, a region of the STIM polypeptide endogenous to the polypeptide serves as a detectable domain (e.g., a region of the polypeptide that can be specifically bound by an anti-STIM antibody). Of particular interest are CBPs composed of a STIM polypeptide modified to contain a detectable domain at the N-terminus, preferably N-terminal of the EF hand domain, wherein the detectable domain is a fluorescent polypeptide.

CBPs of the invention include CBPs in both a precursor form (or "immature" form) as well as in the mature or "processed" form. STIM polypeptides upon which CBPs are based include a signal peptide to facilitate delivery of the polypeptide to the appropriate membrane. This signal peptide is cleaved during processing, and thus is absent in the mature form. Thus, in general, constructs suitable for expression of a CBP in a cell according to the invention include a signal peptide. Because the invention contemplates both constructs suitable for production of a CBP in a host cell, as well as host cells that express the immature and mature forms of the CBP, the invention includes precursor and processed CBPs which contain and lack the signal peptide, respectively.

Generally, where the CBPs are structured to include a heterologous detectable domain, the detectable domain is positioned at the N-terminus of the polypeptide, and usually with the C-terminus of the detectable domain being positioned about 40 to 50 amino acids, usually about 45 amino acids, N-terminal of the EF hand domain. In the precursor form, the heterologous detectable domain is preferably positioned between the signal peptide and the EF hand domain. In general, in the precursor form of CBPs, the signal peptide is provided N-terminal of the detectable domain, which signal peptide is usually from about 20 to 25 amino acids, usually about 22 amino acids. In exemplary embodiments, a region of usually about 30, 35, or 40 amino acids separates the C-terminus of the EF hand domain from the N-terminus of the SAM domain. The C-terminus of the SAM domain is separated from the N-terminus of the transmembrane domain by about 10 to 20 usually about 15 amino acids. The C-terminus of the transmembrane domain is separated from the N-terminus of the ERM domain by about 15 to 25 amino acids, usually by about 20 amino acids.

The detectable domain can be flanked by one or more linkers, which can be for example, from about 5 to 15, from 10 to 15, usually from about 6 to 12 amino acids in length, and can be about 20 amino acids or more, and, where flanking the detectable domain, are selected independently as to length and sequence. Linkers should be selected so that they do not substantially affect function of the CBP, e.g., linkers should lack a functional domain (e.g., a region relatively rich for positively or negatively charged amino acids) that may affect trafficking of the protein.

Any detectable domain known in the art is suitable for use in the calcium biosensor polypeptides of the present invention. A suitable detectable domain will generally be one that can be expressed in a desired host cell and will readily provide a detectable signal that can be assessed qualitatively and/or quantitatively, and can be detected directly or indirectly. Exemplary detectable domains include fluorescent polypeptides, wherein the fluorescent polypeptides include, but are not limited to, yellow fluorescent protein (YFP), cyan fluorescent protein (CFP), GFP, mRFP, RFP (tdimer2), HCRED, and the like, or variants thereof (e.g., fluorescent proteins modified to provide for enhanced fluorescence or a shifted emission spectrum, e.g., enhanced YFP). Further suitable fluorescent polypeptides, as well as specific examples of those listed herein, are provided in the art and are well known. "Fluorescent polypeptide" or "fluorescent polypeptide domain" as used herein is thus meant to encompass wild-type and modified fluorescent polypeptides. Exemplary non-fluorescent detectable domains include immunodetectable epitopes, such as FLAG, His tags, and the like. It should be noted that where the detectable domain is an immunodetectable domain, detection generally involves permeabilizing the cells (e.g., fixing the cells or treating the cells with a detergent) and contacting the cells with a detectably labeled antibody that specifically binds the immunodetectable domain. Alternatively, binding of the anti-immunodetectable domain antibody can be accomplished using a secondary antibody that is detectably labeled.

In some embodiments where multiple CBPs are present in a single cell, the detectable domain of the CBP may be selected so that each CBP in the cell has a detectably different signal. For example, in such embodiments comprising fluorescent polypeptide labels, a first CBP and a second CBP are designed to have detectably distinct emission spectra to facilitate detection of a distinct signal from each biosensor (e.g., through use of different filters in the imaging system).

A "STIM polypeptide" as used herein refers to a polypeptide having the structure of a STIM1 or STIM2 polypeptide or variant thereof which retains function in binding calcium and in formation of a diffuse membrane pattern in cells having a normal level of calcium in intracellular stores and formation of a punctate pattern in cells having a low level of calcium in intracellular stores.

Guidance as to amino acid variations (e.g., amino acid substitutions, deletions, insertions, and the like) in CBPs of the invention can be provided by alignment of the human amino acid sequences of STIM1 and STIM2 with one another (see, e.g., FIG. 10), as well as by alignment of amino acid sequences of STIM1 and/or STIM2 polypeptides with the amino acid sequences of STIM polypeptides that are allelic variants from the same organism or are from other sources. For example, FIGS. 10A-10B provide an alignment of the amino acid sequences of exemplary human STIM1 and human STIM2 precursor polypeptide. The regions of the polypeptides corresponding to the amino acid sequence containing the signal peptide, EF hand domain, SAM domain, transmembrane (TM) domain, and ERM domain of STIM1 are indicated in the figure in bold, with descriptive text over each region. A CBP based on a STIM2 polypeptide can thus be a STIM2 polypeptide modified to contain a detectable domain positioned at the N-terminus, preferably N-terminal to the EF hand domain and, in the precursor form, more preferably between the signal peptide and the EF hand domain. Further, such alignments provide guidance to the ordinarily skilled artisan regarding areas of the amino acid sequences within different portions of the STIM polypeptides that can tolerate amino acid changes (e.g., insertions, deletions, substitutions (e.g., conservative or non-conservative amino acid changes)) without loss of relevant function for production of CBPs of the invention (as well as production of CIMs of the invention, as described in more detail below).

Sequences of a large number of STIM polypeptides have been described For example, the amino acid sequences of STIM polypeptides of human (e.g., STIM1: GenBank Acc Nos. NP_003147.2, HSU52426, NM_003156.2, BC021300.2, AY399210.1; Q13586; STIM2: NP_065911, Q9P246, AAH15659, AAH57231, AAK82337), non-human primate (e.g., STIM1: GenBank Acc. No. AY399211), bovine (STIM1: GenBank Acc. No. BT021898, AAX46745), mouse (e.g., STIM1: GenBank Acc. Nos. MMU47323, AK041944.1, BC021644.1, NM_009287.2, AY399212.1 and P70302, NP_033313, AAH21644; STIM2: XP_132038, P83093, AAH43455, AAK823390), rat (e.g., STIM1: GenBank Acc. No. XM_341896), *drosophila* (e.g., STIM: NP_996470.1), and *C. elegans* (e.g., STIM: NP_741073.1, NP_741074.1) origin are known in the art, as are the amino acid sequence of other STIM polypeptides.

Additional guidance as to amino acid variations in the CBPs of the invention is provided from the knowledge of the functional domains present in the STIM polypeptides that serve as the CBP backbones (see, e.g,. Williams et al., Biochim Biophys Acta. Apr. 1, 2002; 1596(1):131-7; and Wiliamsn et al., Biochem J. Aug. 1, 2001; 357(Pt 3):673-85. For example, EF hand domains are well-characterized and well known in the art. Generally, one or more aspartic acid residues present in the EF hand domain are important for calcium binding, as illustrated in the Examples below with respect to the CIM polypeptide of the invention. The relationship between structure and function in EF hand domains has been studied extensively, and modifications in the amino acid sequences that can be made without affecting calcium binding affinity are well known. See, e.g., Gulati, et al. FEBS Lett. 1989 May 8; 248(1-2):5-8; Kawasaki et al. Biometals. December 1998;11(4):277-95; InterPro Accession Number IPR002048. SAM domains (sterile alpha motif domains) are also well characterized in the art (see, e.g., InterPro Accession Number IPR001660; see also Wiliams et al. Biochim Biophys Acta. Apr. 1, 2002; 1596(1):131-7, discussing analysis of SAM domain in STIM1). ERM domains (E for ezrin, R for radixin and M for moesin) are also well characterized as widespread protein modules that can be involved in localizing proteins to the plasma membrane and crosslinking actin filaments with plasma membranes (InterPro Accession Number IPR000798).

Thus with reference to a CBP polypeptide having a human STIM1 polypeptide as a backbone, the CBPs of the invention can share, for example, 75%, 80%, 85%, 90%, 95% or greater amino acid sequence identity across the portion of the CBP derived from a human STIM1 polypeptide.

Specific exemplary CBPs are described herein based on the amino acid sequence of human stromal interaction proteins (STIM) STIM-1 and STIM-2, e.g., the STIM-1 or STIM-2 polypeptides serve as the backbone for the CBP and are modified to contain a detectable domain. FIGS. 9A and 9B provide the amino acid sequence and encoding DNA sequence of an exemplary CBP based on the amino acid sequence of human STIM1 (referred to as "SP-YFP-STIM1"). FIG. 9A indicates the various portions of the amino acid sequence correspondence to the signal peptide, linker sequences, enhanced YFP, EF hand, SAM domain, transmembrane domain, and ERM domain (indicated by brackets). In this example, the detectable domain is provided by an enhanced YFP, which is positioned between the signal peptide and the EF hand domain of the STIM1 protein. As illustrated in FIG. 9A, The enhanced YFP is flanked by linker sequences, which were used to facilitate insertion of the enhanced coding sequence into the STIM1 coding sequence.

The invention also contemplates a CBP based on a STIM2 polypeptide, particularly a human STIM2 polypeptide.

Calcium-Inseneitive Markers

In general, calcium-insensitive markers (CIM) of the present invention are fusion proteins comprising: 1) a signal peptide (in the precursor form), 2) a detectable domain, usually a heterologous detectable domain, such as a fluorescent polypeptide domain; and 3) a mutant EF-hand domain, which is modified to have a decreased binding affinity for calcium, 4) a SAM domain, 5) a transmembrane domain, and 6) an ERM domain. The modified EF-hand domain causes the CIM to aggregate, thus forming puncta and the punctate pattern, regardless of intracellular stored calcium levels. Accordingly, following expression of the CIM, the CIM will provide a detectable punctate pattern which is not affected by, and thus does not change, with changes in intracellular stored calcium levels.

Except for the EF hand domain, the other domains of the CIM are similar or the same as those for CBPs as described above. The EF hand domain is well characterized, and modifications to provide for decreased binding of calcium relative to an unmodified EF hand domain are known in the art. For example, substitution or deletion of an aspartic acid residue in the EF hand domain, as described in the examples below, can provide for the desired decreased calcium binding affinity.

The CIM and the CBP can be provided in the same or different host cells. Where a CIM and a CBP are provided in the same host cell, e.g., so that the CIM can serve as an internal control and marker of a pattern reflective of low calcium state, the detectable domains of the CIM and the CBP are selected so that the CIM and CBP can be distinguished based on the respective detectable signals. For example, in such embodiments comprising fluorescent polypeptide labels, the fluorescent domain of the CIM is selected to have a different emission spectra compared to that of the fluorescent domain of the CBP to facilitate detection of a distinct signal from each of the CIM and the CBP (e.g., through use of different filters in the imaging system).

Where the detectable domains of the CIM and the CBP are fluorescent, the fluorescent polypeptides can be selected so that two different emission spectra (e.g., two detectably different colors, one from each of the CIM and the CBP) are detected in different patterns (a diffuse pattern for the CBP, and a punctate pattern fro the CIM) when the cell is in a normal calcium state (i.e., not in a low calcium state). When the cell is in a low calcium state, the first and second emission spectra are colocalized due to aggregation of the CIM and the CBP (e.g,. CBP aggregate in puncta with or adjacent the puncta of the CIM). In this way, a decrease in calcium in the cell can be determined by assessing colocalization of two different emission spectra. In general, images of the CBP and CIM patterns are taken using two different channels using a fluorescence microscope, and images processed to overlay the two images (e.g., using a colocalization function commonly found in image processing software). Methods for assessing colocalization of the two images can be accomplished using methods and tools readily available in the art, e.g., MetaMorph™ (Universal Imaging). Colocalization of the CBP and CIM images can be assessed qualitatively or quantitatively.

Accordingly, in one embodiment, the invention provides an array that includes at least one host cell containing a CIM-encoding construct of the invention on at least one defined spot on the array (e.g., within at least one well of a multi-well array). The CIM-containing host cell can serve as a reference cell for a punctate pattern associated with a low level of intracellular calcium stores in the cell. In another embodiment, the invention provides an array that includes at least one host cell containing a CBP-encoding construct of the invention on at least one defined spot on the array (e.g., within at least one well of a multi-well array). In still another embodiment, the invention provides an array that includes at least one host cell containing a CIM-encoding construct and a CBP-encoding construct, where the CIM and the CBP have different detectable domains which provide for distinct signals. In this latter embodiment, the CIM serves as an internal control for the punctate pattern associated with a low intracellular calcium stores in the cell.

Nucleic Acids

The subject invention also provides nucleic acid compositions encoding the calcium biosensor polypeptides (CBP) and calcium-insensitive markers (CIM) described herein, particularly nucleic acids encoding the precursor froms of CBPs and the precursor forms of CIMs, which precursor forms include a signal peptide. Nucleic acid compositions of particular interest comprise a sequence of DNA having an open reading frame that encodes a calcium biosensor polypeptide of the subject invention and is capable, under appropriate conditions, of being expressed as a protein according to the subject invention.

The subject nucleic acids may be present in an appropriate vector for extrachromosomal maintenance or for integration into a host genome, as described in greater detail below. Preferably the subject nucleic acids are provided for stable maintenance in a host cell in which assays are to be conducted, e.g., as a genomic integrant.

The subject polynucleotides and constructs can be generated by a number of different protocols known to those of skill in the art. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are constructs comprising the subject nucleic acids inserted into a vector, where such constructs may be used for a number of different applications, including propagation, protein production, etc. In some embodiments, the vector (e.g., a plasmid) will contain nucleic acid having a coding sequence for a calcium biosensor polypeptide, preferably including a coding sequence of a signal polypeptide positioned at a 5' end of the coding sequence to facilitate appropriate processing and insertion of the CBP in host cell membranes. In other embodiments the vector contains nucleic acid having a coding sequence for a calcium-insensitive marker (CIM), preferably including a coding sequence of a signal polypeptide positioned at a 5' end of the coding sequence to facilitate appropriate processing and insertion of the CIM in host cell membranes. In other embodiments, where a CBP and CIM are co-expressed in a host cell, a single vector contains nucleic acid containing a sequence encoding a CBP and a CIM of the invention (e.g., in two different expression cassettes). Alternatively, the CBP and CIM are provided on two different vectors Viral and non-viral vectors may be prepared and used, including plasmids, which provide for replication of CBP- and/or CIM-encoding DNA and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells, particularly stable expression, in culture. The choice of appropriate vector is well within the skill of the art. Many such vectors are available commercially. Methods for production of such vectors are well known in the art.

Also provided are expression cassettes or systems that find use in, among other applications, the synthesis of the subject proteins. For expression, the gene product encoded by a polynucleotide of the invention is expressed in any suitable host cell in which detection of calcium signaling modulation is desired, e.g., eukaryotic cells, including mammalian, insect, amphibian and avian cells, and the like. In the expression vector, a subject polynucleotide is operably linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated (e.g., inducible) or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Eukaryotic promoters suitable for use include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gal1 gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters may be, furthermore, either constitutive or regulatable. Inducible elements are DNA sequence elements that act in conjunction with promoters and may bind either repressors (e.g. lacO/LAC Iq repressor system in *E. coli*) or inducers (e.g. gal1/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below. Alternatively, expression vectors can take advantage of recombination systems (e.g., Cre-lox, att sites, and the like) to provide for manipulation of vector components. Exemplary systems include the Creator™ (Clontech) and Gateway™ (Invitrogen) systems.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

The above described vector systems may be employed with prokaryotes or eukaryotes in accordance with conventional ways. Generally, it is desirable to express the gene in eukaryotic cells, particularly mammalian cells, where the expressed protein are provided in association with a membrane of a sequestered calcium store, e.g., a membrane of an endoplasmic reticulum. Expression in bacterial cells may be desired where purification of the protein may be of interest (e.g., for production of antibodies, particularly monoclonal antibodies and antigen-binding fragments thereof, e.g., to provide a reagent for detection of a detectable domain of the CBP or CIM, which may be endogenous or heterologous to the STIM polypeptide backbone of the CBP or CIM).

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism.

The subject nucleic acids may be mutated in various ways known in the art to generate targeted changes in the sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Techniques for in vitro mutagenesis, including site specific mutagenesis of cloned polynucleotides are known. Nucleic acids that differ in nucleotide sequence but encode the same amino acid sequence due to the degeneracy of the genetic code are also contemplated, and are referred to herein as "degenerate variants". In some embodiments where the CBP or CIM encode sequences that are of a different origin than the host cell in which the construct is to be expressed, it may be desirable to provide for selection of codons for optimal expression in a particular host cell, e.g., to provide a human-optimized nucleic acid that utilizes codons most frequently used in a human cell.

Recombinant Cells

The invention also features host cells engineered to express a CBP and/or CIM of the invention, as well as kits and methods of the subject invention using such cells. Of particular interest are recombinant host cells that are modified to provide for stable expression of a CBP, of a CIM, or of both a CBP and a CIM according to the invention.

While use of the methods and compositions of the invention find particular use in mammalian cells, particularly human cells, the CBPs and CIMs can be used in connection with any eukaryotic cells that normally contain a calcium-responsive STIM polypeptide (Williams et al., (2001) Biochem. J., 357, 673-85).

In general, the subject cells are eukaryotic cells that support production of a CBP and/or CIM, according to the invention. Preferably, the cells are such that can be readily propagated in culture and readily manipulated using recombinant techniques. Exemplary cells, include, but are not necessarily limited to, mammalian cells (particularly human cells), such as Jurkat (human T-lymphocyte) E6-1 cells, HeLa cells, and the like. In some embodiments, the cells are obtained from a patient having a defect in a calcium signaling pathway or defect in calcium mobilization (e.g., a defect associated with SOC influx). Cells suitable for use in the invention include cell lines (e.g., immortalized cells) as well as primary cells that are amenable to recombinant manipulation.

In general, the cells are generated by introduction of one or more constructs for expression of a CBP and/or CIM of the invention. As described in greater detail above, in some embodiments a single polynucleotide e.g., plasmid, may encode one or more CBPs, or may encode a CBP and a CIM. In other embodiments, a CBP and CIM are provided on separate constructs for introduction into the host cell.

The constructs can be introduced into the host cell by any one of the standard means practiced by one with skill in the art to produce a recombinant cell of the invention. The nucleic acid constructs can be delivered, for example, with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like.

In some embodiments, the CBP and/or CIM are introduced into the cell as polynucleotides encoding the CBP and/or CIM for transient expression (e.g., the vector is maintained in an episomal manner by the cell). In other embodiments, one or more expression constructs encoding a CBP and/or CIM can be stably integrated into a cell line. In addition or alternatively, a polynucleotide encoding a CBP or CIM can be stably integrated into the cell, while a CIM or CBP can be optionally carried on one or more transient expression vectors. For example, a polynucleotide encoding a CIM may be stably integrated in the cell line, a while a polynucleotide encoding CBP is carried on a transient expression vector, or vice versa.

Methods of Using Biosensor Polypeptides

As mentioned above, the subject biosensor polypeptides find particular utility in assays designed to monitor intracellular calcium stores, which in turn yields information about the cell's physiological state with respect to intracellular calcium levels, as well as with respect to SOC influx. In addition, the subject calcium biosensor polypeptides also find particular utility in screening assays designed to identify an agent (e.g., a gene product or small molecule compound) that modulates the intracellular stored calcium levels of a eukaryotic cell.

Monitoring Intracellular Calcium Stores

Expression of a CBP in a variety of cell lines allows monitoring of intracellular calcium stores. When calcium stores are replete with calcium, the CBPs will be bound to calcium, and will provide a diffuse pattern when detected. When calcium stores are depleted, the CBPs are not bound to calcium and will provide a punctate pattern. One can monitor these changes in intracellular stores of calcium over time (e.g., over seconds to several minutes, e.g., 30 s, 60 s, 90 s, 120 s, 150 s, 180 s, 210 s, 240 s, 300 s, 360 s, or longer), such that in a series of detections, the cell will proceed from diffuse detectable pattern to punctate detectable pattern, or vice versa.

Determining a Cell's Physiological State with Respect to SOC Influx

The state of intracellular calcium stores gives information about the cells state of SOC influx. When calcium stores are depleted, and the CBPs detectable pattern is punctate, the cell is in a physiological state of SOC influx (i.e., it is expected that a normal cell will undergo an influx of calcium from the extracellular space into the cytoplasm, assuming the cell is not in a calcium-depleted environment). When calcium stores are replete, and the CBPs detectable pattern is diffuse, the cell is not in a physiological state of SOC influx.

Using Combinations of CBPs to Monitor Intracellular Calcium Stores

One or more CBPs of the subject invention can be used individually to monitor the calcium biosensor state or the cell's state of calcium influx. Accordingly, in some embodiments, a calcium biosensor polypeptide comprising a STIM1 polypeptide having a detectable domain may be used in conjunction with a calcium biosensor polypeptide comprising a STIM2 polypeptide having a detectable domain. Patterns for both of these calcium biosensor polypeptides can be used to assess a cell's intracellular stored calcium levels.

Assessing Effects of Agents with Known or Unknown Activity in Modulating Calcium Signaling The invention provides for identifying agents that modulate calcium signaling through a variety of mechanisms, as well as assessing the effects of agents having known activity in calcium signaling modulation upon particular stages of calcium store mobilization (e.g., calcium store depletion, SOC influx, calcium store replenishment, and the like). For example, the assays of the invention can facilitate identification of agents that directly modulate calcium signaling, e.g., by modulating activity of a cell surface protein (e.g., receptor or channel) that has a direct effect upon calcium signaling or transport). The assays of the invention can also facilitate identification of agents that indirectly modulate calcium signaling, e.g., by affecting an event upstream or downstream of a cellular event responsible modulating a calcium signaling pathway.

The invention also facilitates determining the stage of calcium mobilization the agent affects. For example, because the CBP punctate pattern occurs after store calcium depletion, but prior to SOC influx which replenishes stores, the assays of the invention can be used to dissect whether the agent facilitates calcium depletion or inhibits SOC influx or replenishment of store calcium. The assays of the invention also allow for determining whether an agent is a reversible or irreversible modulator.

Monitoring Intracellular Calcium Stores Using a Calcium-Insensitive Marker

One or more CBPs of the subject invention can be used in conjunction with a calcium-insensitive marker (CIM) of the subject invention, wherein the calcium-insensitive marker provides for a punctate pattern irrespective of the intracellular stored calcium levels. In such an embodiment, the CBP and CIM must have different detectable domains that allow one to discriminate between the CBP and the CIM. For example, the CIM can comprise a detectable domain of a first fluorescence spectra (e.g., yellow), which provides a calcium-insensitive punctate pattern in the cell. The CBP comprises a detectable domain of a second fluorescence spectra different from the fluorescence spectra of the CIM (e.g., blue). When intracellular calcium store levels become depleted, the CBPs comprising blue fluorescence aggregate with or adjacent the puncta of the CIM. When the images of the CBP and CIM patterns are overlaid by image processing, the image can be processed so as to represent overlap of the two signals as a third color. Thus, colocalization of the CBP and CIM indicates a depletion of calcium stores. Likewise, separation of CBP and CIM patterns (due to a decrease in puncta from CBP) indicates normal calcium stores and/or replenishment of intracellular calcium stores.

Methods of Monitoring and Detection of Detectable Domains of CBP and CIM

The methods of the invention are amenable to monitoring cells in culture using any suitable microscopic method. In one embodiment, the detectable domain of the CBP or CIM is fluorescent. Where the detectable domains are immunodetectable, detection can be accomplished using a labeled primary antibody that specifically binds the detectable domain of the CBP or specifically binds the detectable domain of the CIM. Alternatively, the primary antibody can be unlabeled, and binding of primary antibody detected using a secondary labeled antibody. Variations on antibody-based detection systems are known in the art, and can be readily adapted to the invention, as will be apparent to the ordinarily skilled artisan.

Where the detectable domain of the CBP and/or CIM are fluorescent, detection can be accomplished in real time and in live cells, e.g., by video microscopy. Alternatively, the CBP and/or CIM patterns can be detected in fixed cells. For example, cells expressing a CBP (with or without a CIM) can be exposed to an agent or other stimulus for different time periods (e.g., at about 10 s, 20 s, 30 s, 60 s, 90 s, 120 s, 150 s, 180 s, or more, or on the order of several minutes to hours). At the end of the time periods, the cells can be fixed according to a suitable method known in the art (e.g., using a fixative such as paraformaldehye, methanol, or the like). The CBP (and/or CIM) patterns can then be detected by detection of the detectable domain.

Where the detectable domain is a fluorescent polypeptide, methods of measuring and/or monitoring fluorescence are well known in the art. Both qualitative assessments (positive/negative) and quantitative assessments (e.g., comparative degree of fluorescence) may be provided by the present methods. Brightness can be measured using any known method, including, but not limited to, visual screening, spectrophotometry, spectrofluorometry, fluorescent microscopy (e.g., confocal microscopy), etc. In some embodiments, monitoring of fluorescent biosensor polypeptides includes the use of an automated imaging system such as an Axon ImageXpress 5000, which can optionally be equipped with a live cell imaging chamber. Other suitable imaging systems include, but are not limited to, BD Biosciences (Pathway HT); Cellomics (ArrayScan V); Amersham (IN Cell Analyzer 1000; IN Cell Analyzer 3000); Molecular Devices (Discovery-1, Discovery-TMA, ImageXpress), and the like. In general, the best quality images may be obtained by focusing the microscope at the bottom of the cell on a support (e.g., the bottom of the cell contained in a microtiter plate).

In embodiments involving use of fixed cells, the cells can be examined at any appropriate time after fixing, preferably at a time after fixing in which the detectable signal from the detectable domain of the CBP and/or CIM can be readily detected.

Identifying Agents That Modulate Intracellular Calcium Store Levels

As further noted above the subject methods can also be used in screening assays designed to identify an agent (e.g., a gene product or small molecule compound) or other stimulus that modulates intracellular levels of stored calcium. In some embodiments, the modulating agent results in depletion of intracellular stores of calcium, which may subsequently result in SOC influx. In some embodiments, the modulating agent will block depletion of intracellular stores of calcium, which may inhibit SOC influx.

In one embodiment, the subject method is carried out by culturing a cell comprising a CBP in the presence of a candidate agent, wherein the CBP comprises a fluorescent polypeptide as a detectable domain. If the candidate agent modulates intracellular stored calcium such that intracellular stored calcium is depleted, then the CBP will provide a punctate fluorescence pattern. In further embodiments, a candidate agent may modulate the rate of calcium store depletion, wherein the cell cultured in candidate agent is compared to a control in the absence of candidate agent. The rate of puncta formation in the presence of the candidate agent compared to, for example, the rate of puncta formation in the presence of a known calcium modulator can be assessed. Alternatively, the candidate agent can be screened for the ability to modulate the effect of a known calcium modulator. For example, inhibition of, or a decreased rate of, intracellular calcium store depletion in the presence of the agent can indicate an obstructing effect of the candidate agent upon intracellular calcium store depletion by the known calcium modulator. The invention can also involve screening to determine whether a known drug modulates intracellular stores of calcium.

The assays of the invention can also be used to assess whether an agent reversibly or irreversibly modulates calcium signaling, since normally CBP patterns can change in live cells from diffuse to punctate and back again, or form punctate to diffuse and back. Similarly, the assays can be adapted to assess the effect of an agent upon modulating SOC influx in a cell in a calcium depleted state.

The assays of the invention can also be adapted to assess the effect of a candidate agent to modulate a stimulated response in a cell exposed to a calcium signaling modulator. For example, the assays of the invention can be conducted using cells exposed to an agonist of a calcium signaling pathway, where the agonist may be added to the cells prior to or at about the same time as the candidate agent. For example, the methods of the invention can be adapted to assess the effects of a candidate agent upon calcium signaling in the presence of an agonist or an antagonist (including inverse agonist) of a GPCR, where the GPCR stimulates directly or indirectly a calcium signaling pathway which modulates calcium stores and/or calcium influx. The methods of the invention can also be adapted to assess the effects of a candidate agent upon calcium signaling in the presence of an agonist of a T cell receptor or a mast cell receptor. For example, where a GPCR agonist causes calcium store depletion, the CBP pattern will be punctate, and assays can be conducted to assess the effect of candidate agents upon inhibiting CBP puncta formation (and thus inhibit calcium store depletion in the presence of the agonist), or which inhibit return of CBP to a diffuse pattern (and thus inhibit replenishing of calcium stores after a period of time after which the cell should recover from the effects of the agonist).

In further embodiments, the subject method is carried out by culturing a cell comprising a CBP that comprises a fluorescent polypeptide, wherein the calcium store depletion is activated using a known activation agent, and wherein the cell is in a calcium depleted environment. Thus, the CBP will provide for punctate pattern that does not revert to diffuse pattern because the cell is in a calcium depleted environment. Candidate agent is then added to the cell environment, and this is followed by returning calcium to the environment. If the punctate pattern does not revert to a diffuse pattern, then the candidate agent is blocking SOC influx. Similarly, if the punctate pattern does revert to a diffuse pattern, then the candidate agent does not block SOC influx.

As noted above, all assays described herein can be conducted with live cells. Alternatively, after a time sufficient for formation of a CBP pattern in response to a stimulus, the cells can be fixed, and detection of CBP or CIM patterns assessed. The use of fixed cells finds particular application in candidate agent screening assays. In general, the cells of the invention are contacted with a candidate agent, and, after a desired time period, the cells are fixed and the CBP and/or CIM patterns in the presence the agent (or, as a control, in the absence and/or different concentrations of the agent) detected. For example, cells expressing a CBP (with or without a CIM) can be exposed to an agent or other stimulus for different time periods (e.g., at about 10 s, 20 s, 30 s, 60 s, 90 s, 120 s, 150 s, 180 s, or more, or on the order of several minutes to hours). At the end of the desired time periods, the cells can be fixed according to a suitable method known in the art (e.g., using a fixative such as paraformaldehye, methanol, or the like). The CBP (and/or CIM) patterns can then be detected by detection of the detectable domain.

Use of fixed cells has several advantages. For example, once the cells are fixed, detection of the pattern of CBP distribution is not as time sensitive as in live cells. Detection of CBP or CIM using fixed cells can take advantage of detection systems that are not as amenable to use in live cells, e.g., antibody-based detection systems. Also, use of fixed cells in the assays of the invention make the assays very amenable to high throughput, since many different assays can be run in parallel and the results of those assays examined at a later time point.

Assays of the invention make it possible to identify agents (such as a gene product or a compound) which ultimately: (1) have a positive effect with respect to modulating intracellular stores of calcium and as such are potential therapeutics, e.g. agents which promote or arrest SOC influx and consequent cell function; or (2) have an adverse affect with respect to intracellular calcium stores and as such should be avoided as therapeutic agents (e.g., to screen candidate agents for toxicity to eukaryotic cells).

Generally a plurality of assay mixtures is performed in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel using a large number of cell populations. By "large number" is at least 10 to 50, usually at least 100, and more usually at least 1000.

Of particular interest in certain embodiments is the use of the subject methods in a high throughput toxicity screening assays. In such high throughput screening (HTS) assays, a plurality of different compound compositions, usually at least 10 different compound compositions, are simultaneously assayed for their activity, if any. Each compound composition in the plurality is assayed for activity by contacting it with a cell comprising the subject biosensor polypeptides and determining the effect of the compound composition on intracellular stored calcium levels.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

The above screening methods may be part of a multi-step screening process of evaluating candidate agents for their efficacy (and safety) in the treatment of autoimmune disease, inflammatory disease (e.g., allergy, asthma, and the like), immunodeficiency (e.g., inherited or acquired immunodeficiency, said, and the like), chronic diseases associated with calcium influx (e.g,. Alzheimer's), and the like in mammalian hosts, e.g. humans. Candidate agents can also be screened for their effects upon T cells (particularly cytotoxic T cells), mast cells or other immune cells that modulate calcium signaling.

In multi-step screening processes of the subject invention, a candidate compound or library of compounds is subjected to screening in a second in vivo model, e.g. a mouse model, following screening in the subject cell lines. Following the initial screening in the cell lines of the subject invention, the positive compounds are then screened in non-human mammalian animal models. In addition, a pre in vivo screening step may be employed, in which the compound is first subjected to an in vitro screening assay for its potential as a therapeutic agent in the treatment of disease or condition of interest. Any convenient in vitro screening assay may be employed, where a variety of suitable in vitro screening assays are known to those of skill in the art.

In some embodiments, the subject methods are useful for identifying a endogenous gene product that has an activity in modulating the intracellular stores of calcium and/or have activity in modulating store operated calcium influx. Genes that have a beneficial effect on the phenotype when their activity is modulated through mutation encode proteins that represent therapeutic targets for the development of compounds that inhibit the function of the protein. Gene based therapies can be identified by doing traditional enhancer/suppressor analyses in the subject cells. In these analyses, genes in the subject cells are mutated to identify ones that either promote or inhibit depletion of intracellular calcium stores. Methods of mutating genes and carrying out enhancer/suppressor analyses are well known to those of skill in the art (Hays, T S et al., Molecular and Cellular Biology (March 1989) 9(3):875-84; Deuring, R; Robertson, B; Prout, M; and Fuller, M T. Mol. Cell. Biol., 1989 9:875-84; Fuller, M T et al., Cell Mot. Cyto. (1989) 14:128-35; Rottgen G, Wagner T, Hinz U Mol. Gen. Genet. 1998 257:442-51). In some embodiments, siRNA is used to disrupt the expression of an endogenous gene to determine whether the endogenous gene had an effect on modulating the levels of intracellular stored calcium.

Automated Screening Methods

The methods of the present invention may be automated to provide convenient, real time, high volume methods of screening compounds for activity in modulation of intracellular calcium stores. Automated methods are designed to detect changes in the pattern of the detected signal (usually fluorescence) of one or more of the biosensor polypeptides over time (i.e., comparing the same apparatus before and after exposure to a test sample), or by comparison to a control apparatus, which is not exposed to the test sample, or by comparison to pre-established indicia. Both qualitative assessments (positive/negative) and quantitative assessments (e.g., concentration of test sample required to promote or inhibit calcium store depletion) may be provided by the present automated methods.

An embodiment of the present invention includes an apparatus for detecting changes in intracellular stored calcium levels according to the subject methods of the present invention. This apparatus comprises means, such as a fluorescence measurement tool, for measuring change in the pattern of detectable signal, such as a fluorescence pattern, associated with one or more CBPs in a eukaryotic cell in response to a particular candidate agent.

Measurement points may be over time, or among test and control samples. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool is preferably operatively coupled to a general purpose or application specific computer controller. The controller preferably comprises a computer program produced for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Kits and Systems

Also provided by the subject invention are kits and systems for use in practicing the subject methods, where the subject kits can include elements for making the subject biosensor polypeptides, e.g., a construct comprising a vector that includes a coding region for the subject biosensor polypeptides. In some embodiments, the subject kits and systems can include, in separate compartments or containers, one or more of the following: 1) one or more constructs encoding one or more of the CBPs or CIMs of the invention; 2) a candidate agent; and 3) a cell containing an expression construct for producing one or more of the CBPs and/or CIMs of the invention. The components of the kits may be modified commensurate to the disclosure provided above.

The subject kit components are typically present in a suitable storage medium, e.g., buffered solution, typically in a suitable container. In certain embodiments, the kit comprises a plurality of different vectors each encoding the subject protein, where the vectors are designed for expression in different environments and/or under different conditions, e.g., constitutive expression where the vector includes a strong promoter for expression in specific eukaryotic cells, a promoterless vector with a multiple cloning site for custom insertion of a promoter and tailored expression of a biosensor polypeptide, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the examples below.

Cell Transfection, Plasmids and Reagents

Figure 11:
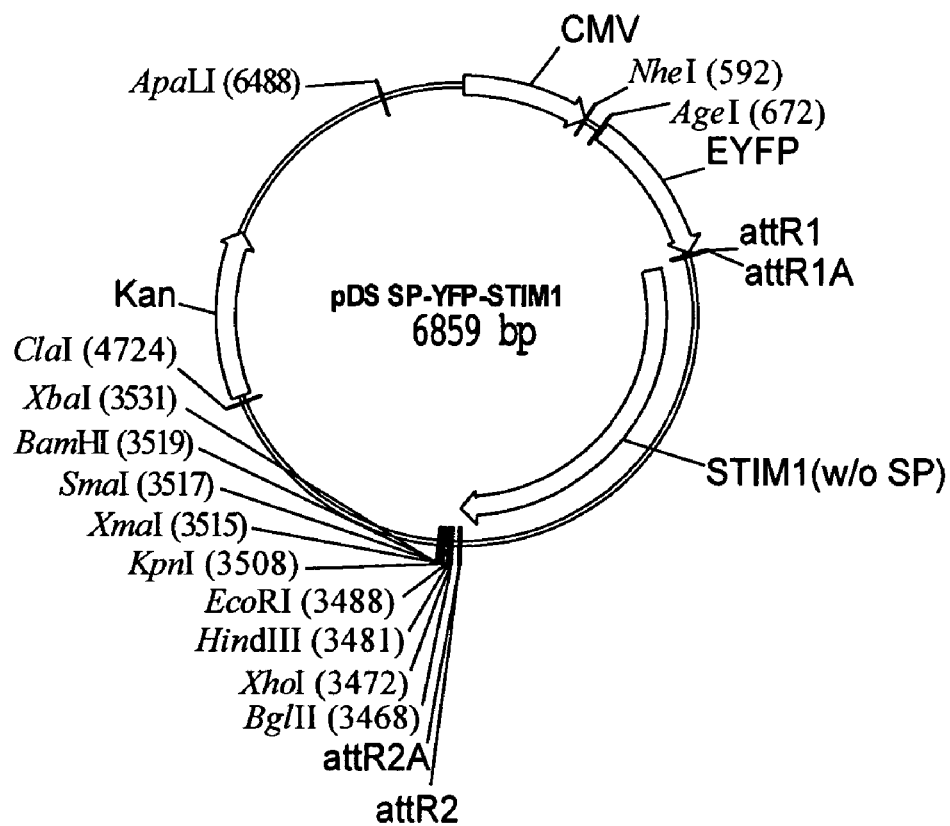
FIG. 11 is a schematic of an exemplary vector encoding a CBP of the invention. A nucleic acid encoding a signal peptide is inserted upstream showing the relative locations in the encoded protein of the signal peptide, detectable domain polypeptide, and STIM1 polypeptide.

HeLa (human epithelial) cells and Jurkat (human T lymphocyte) E6-1 line were purchased from ATCC. DNA plasmids and siRNA were co-transfected into HeLa or Jurkat cells using Genesilencer reagent (Gene Therapy Systems, San Diego, Calif.). Full-length human STIM1 cDNA was isolated by PCR, sequenced and cloned in to pDS_XB-YFP vector (ATCC). Enhanced yellow fluorescent protein (YFP) or cyan fluorescent protein (CFP) (Clontech, Palo Alto) was inserted immediately downstream of the predicted signal peptide region of human STIM1. FIG. 11 provides a schematic of the SP-YFP-STIM1 construct used in the Examples below.

The YFP-conjugated EF-hand mutant of STIM1, YFP-STIM1(D76A), was made by site-directed mutagenesis using the QuikChange Site-Directed Mutagenesis Kit (Stratagene). Nucleotide sequences of constructs were verified by sequencing. The amino acid and DNA sequence of the SP-YFP-STIM1 polypeptide used in the Examples below are those provided in FIGS. 9A and 9B, except that the last valine in the ERM domain may be alanine. NF-ATc1-YFP was provided by Dr. Won Do Heo. pECFP-Nuc, pECFP-ER, and pEYFP-Nuc plasmids were purchased from Clontech Inc. pECFP-CAAX plasmid was provided by Dr. Mary Teruel.

Thapsigargin, histamine, and BHQ (2,5-di-(t-Butyl)-1,4-benzohydroquinone) were purchased from Calbiochem. Anti-human CD3 (T-cell receptor) antibody (BD BioSciences) was used at 20 μg/ml. SKF 96365 (Sigma) was used at 20 μM.

siRNA Library of Signaling Proteins 2,304 human signaling-related proteins were selected from the National Center for Biotechnology Information (RefSeq database) based on the presence of signaling domains, such as protein kinase, SH2, SAM, EF and PH-domains, as well as by text searches of signaling related terms. Gene-specific primers for the selected signaling proteins were designed using an in-house primer program, and were used to generate ~600 bp cDNA fragments immediately upstream of the stop codon of each mRNA by PCR. An additional set of nested primers was designed to add T7 promoters at both ends of the final cDNA fragment. Nested PCR products were subjected to in vitro transcription, in vitro dicing, and purification to produce siRNA as described previously (Myers et al., (2003) *Recombinant Dicer efficiently converts large dsRNAs into siRNAs suitable for gene silencing,* Nat. Biotechnol. 21, 324-328). The siRNA signaling set was sorted according to the NCBI RefSeq Protein accession number, and was stored in twenty-four 96-well plates. The screen for SOC influx regulators was done by transfecting HeLa cells with the siRNA signaling set at an average concentration of 10 nM for 2 days in the 96-well format. 24 siRNAs present in duplicates were screened at a time in an experimental microplate. The whole screen was performed twice.

$Ca^{2+}$ Measurements $Ca^{2+}$ measurements were made with a fluorescence microplate reader (FlexStation, Molecular Devices). HeLa cells were loaded with 2 μM Fura-2-AM in extracellular buffer (125 mM NaCl, 5 mM KCl, 1.5 mM $MgCl_2$, 20 mM HEPES, 10 mM glucose, and 1.5 mM $CaCl_2$, pH7.4) for 30 min at room temperature. Fura-2 fluorescence was measured by illuminating the cells with an alternating 340/380 nm light every 5 seconds. Fluorescence intensity was measured at 510 nm. Changes in intracellular $Ca^{2+}$ concentration are presented as the change in the ratio of fluorescence intensity for excitation at 340 and 380 mn. For $Ca^{2+}$ add-back experiments, 3 mM EGTA was added together with histamine and thapsigargin to remove extracellular $Ca^{2+}$, and 10 mM $Ca^{2+}$ was added back following $Ca^{2+}$ store depletion. Imaging-based single cell $Ca^{2+}$ measurements of HeLa or Jurkat cells were performed using a 4× (HeLa) or 10× (Jurkat) objective on an automated fluorescent microscope ImageXpress 5000A (Molecular Devices) by loading cells with 0.5 μM Fura-2-AM. Fluorescence intensities of single cells were measured using the ImageXpress analysis software.

$Mn^{2+}$ Quench Assays 2 mM $Mn^{2+}$ was added to cells immediately before image acquisition. Histamine and thapsigargin were added 50 seconds after, and image acquisition was continued for another 90 seconds. Quenching of Fura-2 fluorescence was measured by illuminating cells with 360 mn light every 4 seconds and fluorescence intensity was measured at 510 nm using the ImageXpress.

Fluorescence Imaging

NF-ATc1 translocation was monitored in HeLa cells co-transfected with NF-ATc1-YFP and pECFP-Nuc plasmids with ImageXpress 5000A using a 10× objective. Live-cell confocal imaging experiments were performed with transfected HeLa cells using a 40× objective on a spinning disk confocal microscope (Nipkow Wallac system). Live-cell TIRF imaging was done with transfected HeLa cells using a 60× objective on a Nikon TIRF microscopy system. Images were analyzed using the MetaMorph software (Universal Imaging Corporation).

Example 1

Identification of STIM1 and STIM2 as SOC Influx Mediators

To identify proteins involved in the SOC influx pathway, 2,304 proteins were selected that contain known signaling domains from the NCBI database and diced siRNAs were generated in vitro against each of the targets. Their role in $Ca^{2+}$ signaling was tested using a kinetic $Ca^{2+}$ screen in an automated microplate reader. Stimulation of HeLa cells with histamine and thapsigargin leads to an initial peak in cytosolic $Ca^{2+}$ levels followed by a plateau. The sustained plateau level is indicative of induced SOC influx. Thus, by monitoring which siRNA reduces the sustained plateau phase without changing the initial peak response, proteins that mediate SOC influx could be identified.

Using visual inspection of the $Ca^{2+}$ time-courses (FIG. 1, Panel A) and comparing the relative $Ca^{2+}$ plateau values (FIG. 1, Panel B), the siRNAs targeting the gene products STIM (stromal interaction molecule) 1 and STIM2 stood out in their ability to suppress the sustained $Ca^{2+}$ signals while at the same time showing little effect on the peak amplitude. While STIM1 and STIM2 were identified previously as potential tumor growth suppressors (Sabbioni et al., (1997) *Cancer Res.* 57, 4493-97; Parker et al., (1996) *Genomics* 37, 253-56; Williams et al., (2002) *Biophys. Acta* 1596, 131-37), they had not been suspected of having a role in $Ca^{2+}$ signaling. Nevertheless, both proteins have been biochemically characterized and have been shown to form homo- and hetero-oligomers as well as to have a transmembrane domain and a putative luminal single EF-hand $Ca^{2+}$-binding domain (Williams et al., (2001) *Biochem J.* 357, 673-85; Williams et al., (2002) *Biophys. Acta* 1596, 131-37; Manji et al., (2000) *Biophys. Acta* 1481, 147-55.) (FIG. 1, Panel C). Both STIM1 and STIM2 are ubiquitously expressed in various mammalian cell types and homologous proteins can be found in *Caenorhabditis elegans* (I copy) and *Drosophila melangoster* (1 copy), two model organisms in which store depletion activated $Ca^{2+}$ influx has been reported.

Example 2

Suppression of $Ca^{2+}$ Influx in STIM Knockdown Cells

Figure 5:
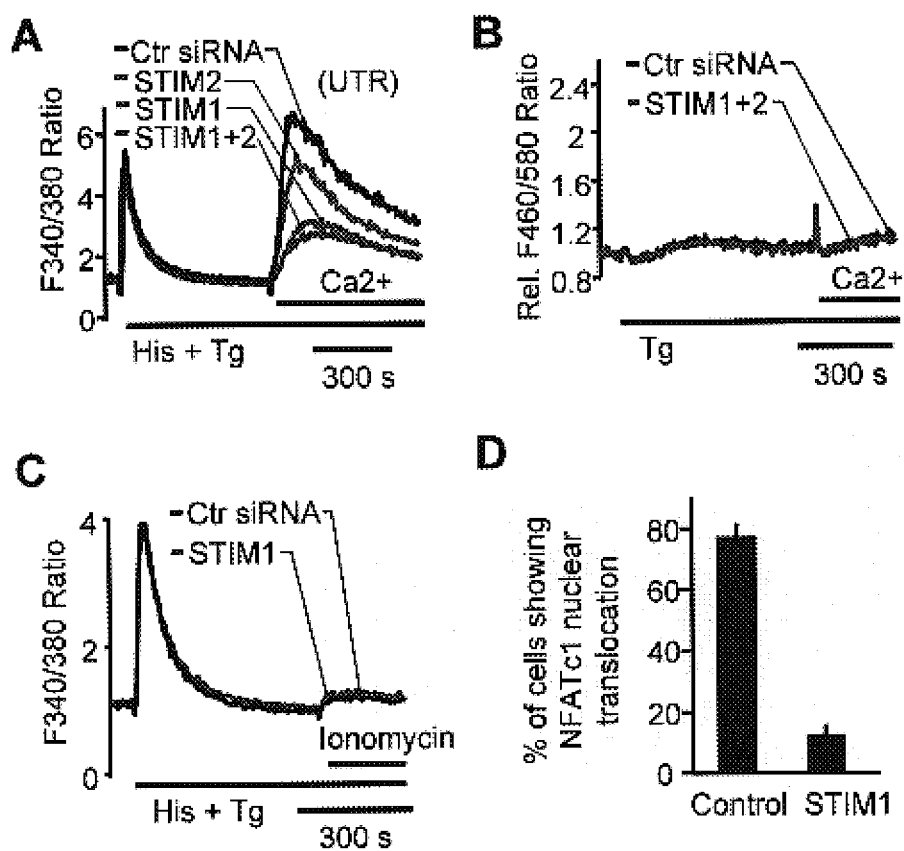
FIG. 5 is a set of graphs showing results of control experiments demonstrating that STIM siRNAs inhibit SOC influx. Panel A: Independent siRNAs against the non-coding region (UTR) of STIM1 and STIM2 were made as controls. Ca$^{2+}$ influx was also suppressed when HeLa cells were transfected with 10 nM STIM1 and/or 10 nM STIM2 UTR siRNA for 2 days and the same Ca$^{2+}$ add-back experiment was performed as in FIG. 1. Panel B: Knockdown of STIM1 does not alter the membrane potential. Membrane potential was measured in HeLa cells transfected with 40 nM control or STIM siRNA using the voltage sensor probes CC2-DMPE and DiSBAC$_2$(3) (Invitrogen) based on manufacturer's instructions. The probe was calibrated by K$^+$ addition (Nernst equation). The membrane potential traces of control and STIM knockdown cells were nearly identical and the estimated changes were less than 10 mV when cells were treated using the Ca$^{2+}$ add-back protocol. Panel C: As in Panel A except that 40 nM of STIM1 siRNA was used and that 5 μM ionomycin was added instead of Ca$^{2+}$ to examine the extent of store depletion. No significant difference in residual store loading was observed in cells transfected with control versus STIM1 siRNA. Data shown in Panels A through C are the average of 3 bulk-cell measurements obtained using a fluorescence microplate reader. Panel D: STIM1 is required for the Ca$^{2+}$ store-depletion triggered nuclear translocation of NF-ATc1. HeLa cells were transfected with 35 ng NF-ATc1-YFP, 5 ng pECFP-Nuc, plus 40 nM STIM1 or control luciferase siRNA and cells were treated with 2 μM thapsigargin under Ca$^{2+}$-free condition and 10 mM Ca$^{2+}$ was added 10 min before image acquisition using an automated fluorescence microscope. Five 10× magnification images of control and five 10× magnification images of STIM1 siRNA transfected cells were analyzed and the percent of cells showing NF-ATc1 translocation in each image were measured. A total of 300 control and 245 STIM1 siRNA transfected cells were monitored. Error bars shown are the standard deviations derived from five measurements.

To confirm that STIM1 and STIM2 are required for the SOC influx pathway, a "$Ca^{2+}$ add-back" experiment was performed in which $Ca^{2+}$ stores were first depleted in the absence of extracellular $Ca^{2+}$ with histamine and thapsigargin. Extracellular $Ca^{2+}$ was then added back to monitor the $Ca^{2+}$ influx. In HeLa cells transfected with siRNA against STIM1, STIM2 or both, a significant suppression of $Ca^{2+}$ influx was observed (FIG. 1, Panel D). The same results were obtained when knockdown cells were stimulated with either histamine alone (FIG. 1, Panel E) or thapsigargin alone (FIG. 1, Panel F). siRNAs against the 3' un-translated regions (UTR) of both STIM1 and STIM2 as well as three synthesized individual siRNAs against STIM1 led to a similar suppression of $Ca^{2+}$ influx (FIG. 5, Panel A). With additional controls, there was no significant difference in membrane potential changes or residual $Ca^{2+}$ in the store between control and STIM1 knockdown cells following stimulation (FIG. 5, Panels B and C). The suppression of $Ca^{2+}$ influx by STIM siRNAs could be titrated as a function of the siRNA concentration (shown for STIM1 in FIG. 1, Panel G). Remarkably, when HeLa cells were treated for 3 days with a combination of 20 nM STIM1 and 20 nM STIM2 siRNA, a significant 6-fold reduction of the SOC influx (to 15% of control siRNA) was observed (FIG. 1, Panel H). This nearly complete inhibition of $Ca^{2+}$ influx shows that STIM proteins have a key role in mediating SOC influx.

Example 3

Suppression of NF-AT Translocation and TCR-Triggered $Ca^{2+}$ Influx by STIM1 siRNA NF-AT is a transcription factor that is activated in response to sustained $Ca^{2+}$ signals (Crabtree et al., (2002) *Cell* 109, S67-79; Beals et al., (1997) *Genes Dev.* 11, 824-34). The activation of NF-AT was monitored to test for a functional consequence of the reduction in SOC influx. Consistent with a functional relevance of STIM1 in NF-AT activation, the translocation of YFP-NF-ATc1 to the nucleus was nearly completely reduced in $Ca^{2+}$ store-depleted HeLa cells transfected with siRNAs against STIM1 compared to control siRNA (FIG. 5, Panel D). SOC influx has been shown to be required for T-cell activation (Lewis et al., (2001) *Annu. Rev. Immunol.* 19, 497-521; Schwartz et al., (2003) *Annu. Rev. Immunol.* 21, 305-34). Thus, the effect of STIM1 on $Ca^{2+}$ influx in a Jurkat T lymphocyte model was examined. This is of therapeutic interest, since a recent study suggested that small molecules that inhibit the T-cells signaling pathway from $Ca^{2+}$ store depletion to $Ca^{2+}$ influx are candidate immunosuppressant drugs (Venkatesh et al., (2004) *Proc. Natl. Acad. Sci. USA* 101, 8969-74). As shown in FIG. 1, Panel B, the SOC influx triggered by T-cell receptor (TCR) stimulation was effectively suppressed by siRNA against STIM1.

Example 4

Regulation of the SOC Influx by STIM

The suppression of $Ca^{2+}$ signals in STIM knockdown cells could in principle result from an accelerated plasma membrane $Ca^{2+}$ extrusion instead of a reduced influx. To distinguish between the two possibilities, the $Ca^{2+}$ influx rate was directly monitored using a $Mn^{2+}$ quench assay (Kass et al., (1990) *J. Biol. Chem.* 265, 17486-92). This method is based on earlier findings that SOC influx channels are permeant to $Mn^{2+}$, and that Fura-2 becomes non-fluorescent when complexed with $Mn^{2+}$. The $Ca^{2+}$ influx rate can thus be measured as the rate of Fura-2 quenching by Mn2+ influx. Consistent with a role of STIM in regulating $Ca^{2+}$ influx and not $Ca^{2+}$ extrusion, siRNAs against a combination of both STIM isoforms suppressed the increase in $Mn^{2+}$ quench rate triggered by $Ca^{2+}$ store depletion (FIG. 2, Panel A).

Human STIM1 was cloned and the protein was conjugated with an N-terminal YFP-tag (after the signal peptide), and the effect of STIM1 overexpression on SOC influx was tested. As shown in FIG. 2, panel B, overexpression of STIM1 significantly increased the SOC influx rate. A small increase in basal $Ca^{2+}$ influx in unstimulated cells was either an artifact of the transient overexpression or evidence that STIM1, at high expression levels, can partially induce $Ca^{2+}$ influx in the absence of store depletion. The increases of SOC and also the basal influx resulting from STIM1 overexpression were almost completely blocked by SKF 96365, an inhibitor of SOC influx (Putney et al., (2001) *Mol. Interv.* 1, 84-94) (FIG. 3, Panel C), providing further support that STIM1 has a role in activating SOC influx.

Example 5

Figure 3:
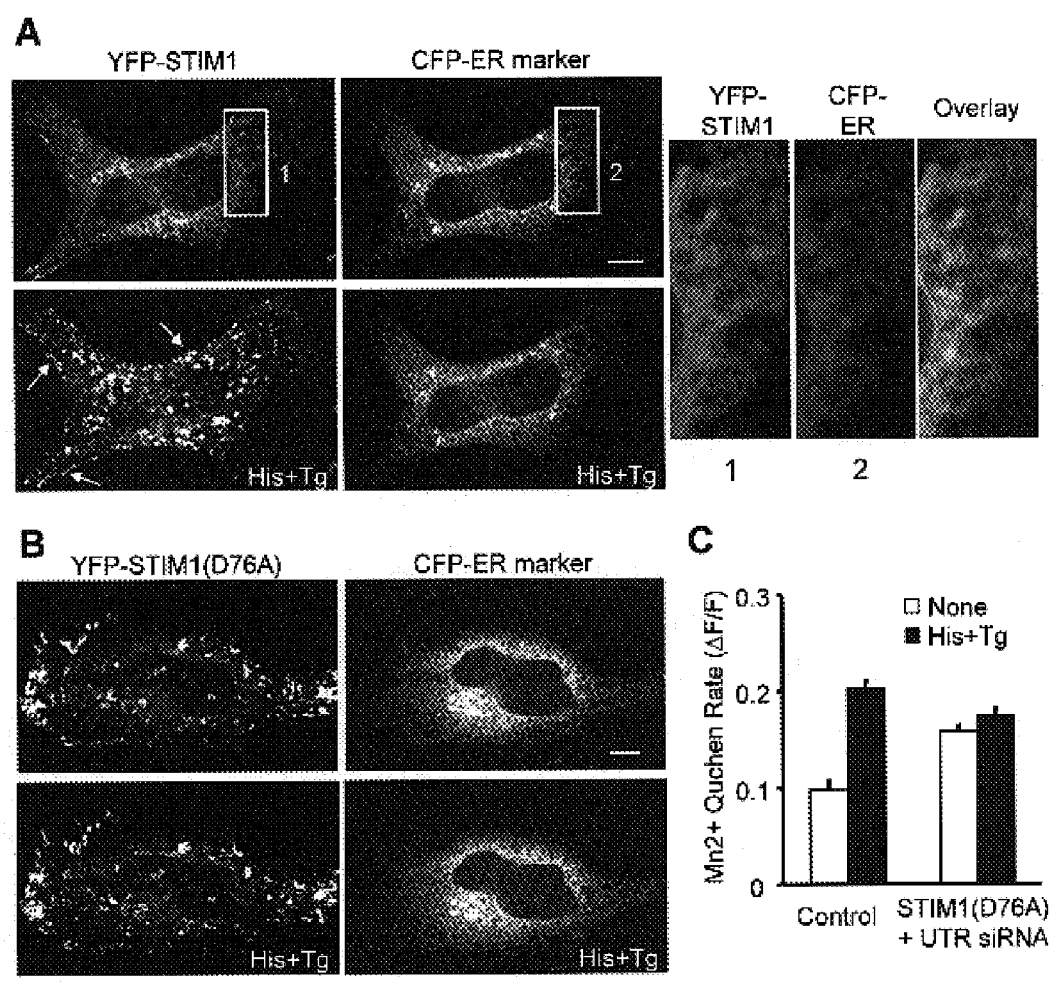
FIG. 3 is a set of photographs and a graphs demonstrating that STIM1 senses ER Ca$^{2+}$ depletion using its luminal EF-hand. Panel A: YFP-STIM1 redistributes into punctate structures following Ca$^{2+}$ store depletion. HeLa cells were co-transfected with YFP-STIM1 and a CFP-tagged ER marker. CFP/YFP confocal images of the same cell were taken before (top two panels) and 8 minutes after (bottom two panels) histamine plus thapsigargin stimulation. The arrows point to peripheral sites rich in puncta. The magnified panels on the right show the co-localization of STIM1 with the ER marker before stimulation. Panel B: The EF-hand mutant of STIM1 is already localized to puncta and does not respond to store depletion. HeLa cells were co-transfected with YFP-STIM1 (D76A) and a CFP-ER marker. CFP/YFP confocal images of the same cell were taken before (top two panels) and 8 minutes after (bottom two panels) histamine plus thapsigargin stimulation. Scale bar=10 μm. Panel C: STIM1 knockdown cells expressing the EF-hand mutant show elevated influx prior to stimulation and are unresponsive to Ca2+-store depletion. Mn$^{2+}$ quench assays were performed in HeLa cells transfected with 40 nM STIM1 UTR or control siRNA plus YFP-STIM1(D76A) or the YFP vector as described in FIG. 2A. Error bars are 95% confidence bounds.
Figure 6:
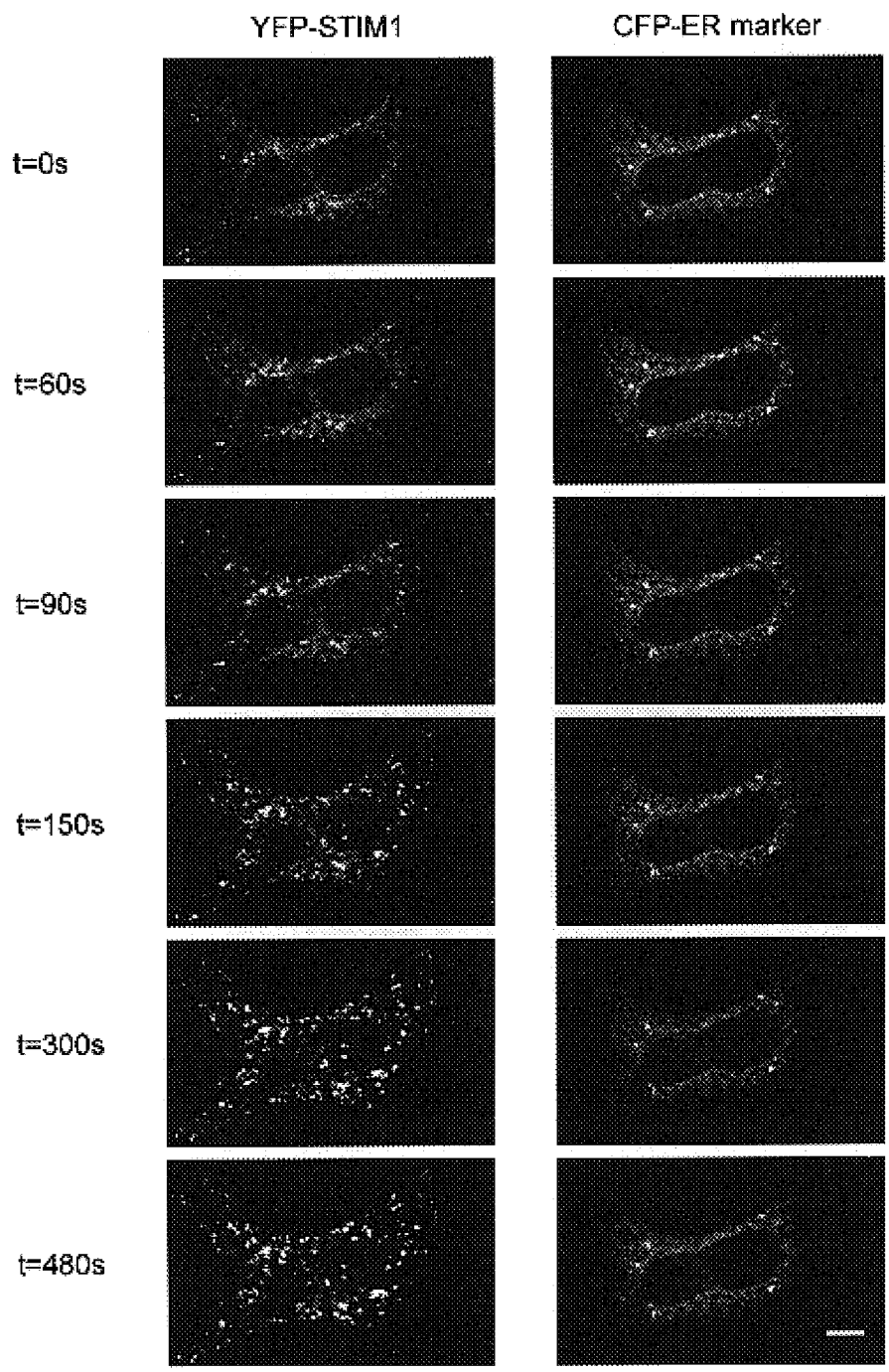
FIG. 6 is a set of photographs showing the kinetics of YFP-STIM1 redistribution following Ca$^{2+}$ store depletion. HeLa cells were co-transfected with YFP-STIM1 and a CFP-ER marker. CFP/YFP confocal images were taken in the same cells at different time points following histamine plus thapsigargin stimulation. Scale bar=10 μm.
Figure 7:
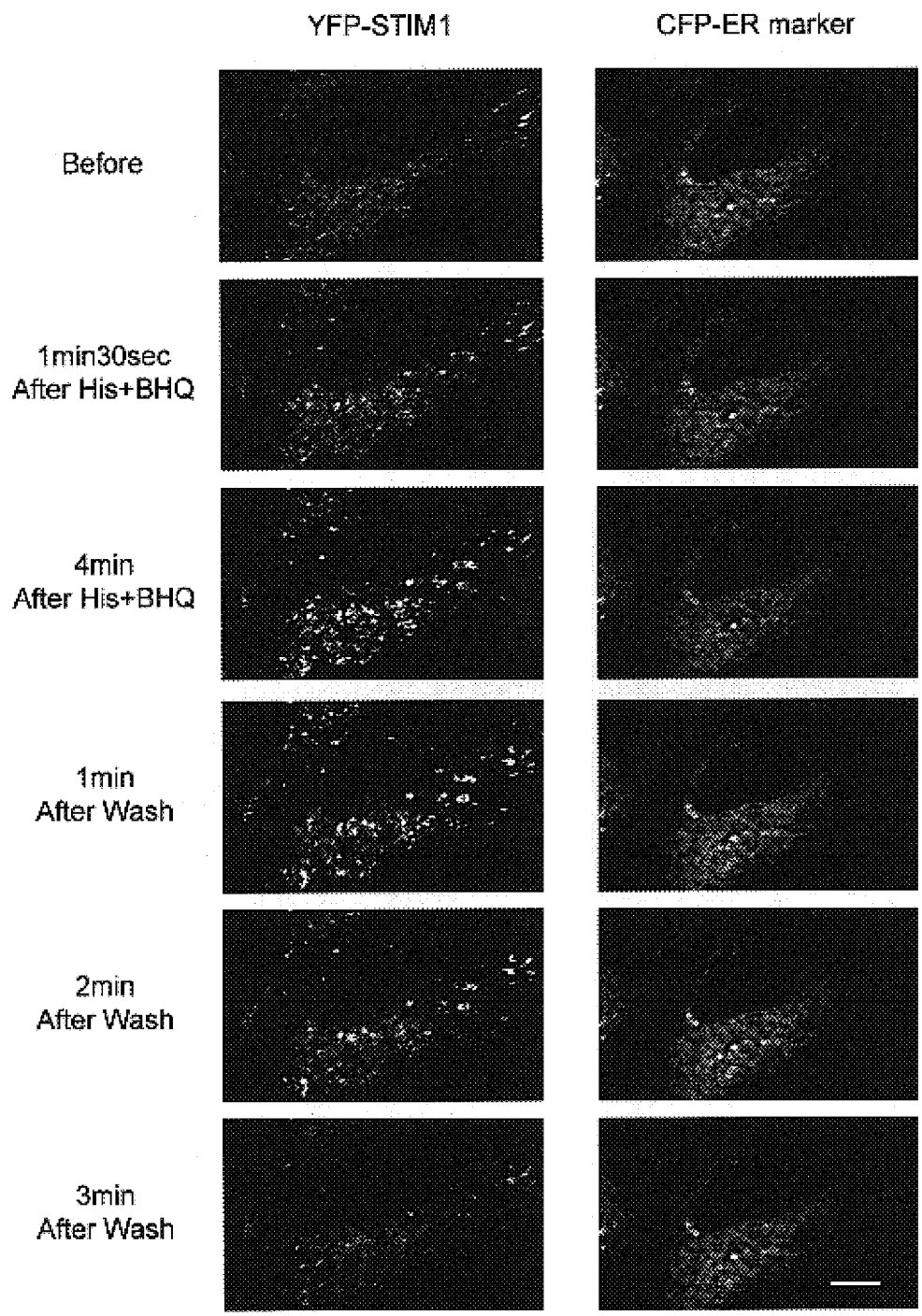
FIG. 7 is a set of photographs showing that YFP-STIM1 puncta formation is reversible. HeLa cells were co-transfected with YFP-STIM1 and a CFP-ER marker. CFP/YFP confocal images were taken in the same cell at different time points. 100 μM histamine plus 5 μM of the ER-pump inhibitor BHQ were used to stimulate cells. Cells were washed twice 6 minutes following stimulation. Scale bar=10 μm.
Figure 8:
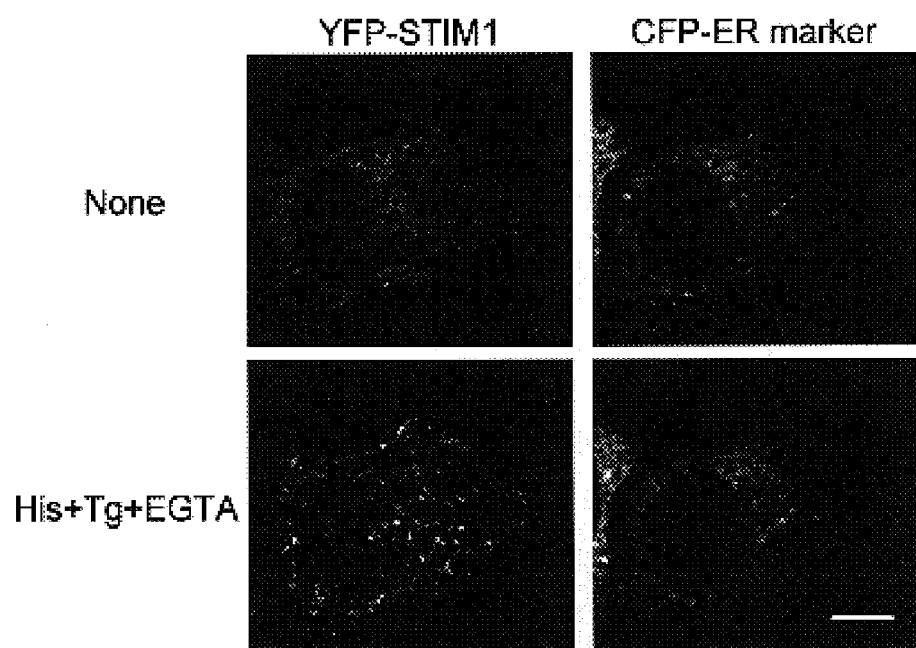
FIG. 8 is set of photographs showing redistribution of YFP-STIM1 to puncta occurs in the absence of extracellular Ca$^{2+}$. HeLa cells were co-transfected with YFP-STIM1 and a CFP-ER marker. CFP/YFP confocal images were taken before (top two panels) and 8 minutes after (bottom two panels) stimulation with 100 μM histamine, 5 μM thapsigargin and 3 mM EGTA. Scale bar=10 μm.

Redistribution of YFP-STIM1 Into Puncta Following $Ca^{2+}$ Store Depletion STIM1 was localized in unstimulated HeLA cells to investigate the mechanism of how STIM proteins regulate the SOC influx pathway. As shown in FIG. 3, Panel A, YFP-STIM1 co-localized with a marker of the endoplasmic reticulum (ER). Strikingly, $Ca^{2+}$ store depletion triggered a redistribution of YFP-STIM1 into puncta that accumulated inside the cell and also appeared to be enriched near the cell periphery (left bottom panel, FIG. 3, Panel A). Initial translocation of YFP-STIM1 could be observed in less than 1 minute (FIG. 6). To test whether this translocation process was reversible, BHQ was used instead of thapsigargin to deplete $Ca^{2+}$ stores and it was found that most YFP-STIM1 puncta disappeared within 3 minutes following the removal of histamine and BHQ (FIG. 7). To test whether some of these puncta are domains within the plasma membrane, the cells were stained for extracellular YFP-STIM1 with anti-GFP antibodies. There resulted no significant insertion of YFP-STIM1 to the plasma membrane after $Ca^{2+}$ store depletion. Furthermore, the redistribution of YFP-STIM1 occurred in the absence of extracellular $Ca^{2+}$ (FIG. 8), showing that the redistribution is likely a cause rather than a consequence of $Ca^{2+}$ influx.

Example 6

The EF-Hand of STIM1 Senses ER $Ca^{2+}$ Store Depletion

Since STIM1 and STIM2 are type-I transmembrane proteins, their unpaired EF-hand domains are predicted to be in the lumen of the ER. This leads to the hypothesis that STIM proteins function as $Ca^{2+}$ sensors that use their EF-hand domains to monitor the loading of $Ca^{2+}$ stores. Interestingly, when the first $Ca^{2+}$-binding aspartic acid residue in the EF-hand (Kawasaki et al., (1998) *Biometals* 11, 277-95; Gulati et al., (1989) *FEBS Lett.* 248, 5-8) was mutated to alanine (D76A), this YFP-STIM1 EF-hand mutant was already significantly pre-localized in puncta before stimulation, and Ca²⁺ store depletion had no significant additional effect on the localization of the EF-hand mutant (FIG. 3, Panel B). The function of the EF-hand mutant was further tested by examining its effect on the SOC influx rate in STIM1 knockdown cells, in which the effects of the endogenous STIM1 are minimized. Consistent with the imaging results, expression of the EF-hand mutant increased Ca²⁺ influx even if the Ca²⁺ stores were filled, and failed to further promote SOC influx in response to Ca²⁺ store depletion (FIG. 3, Panel C). Notably, the EF-hand mutant could not completely restore SOC influx level in knockdown cells, which indicates that prolonged activation of STIM leads to a partial desensitization of SOC influx.

Example 7

Two Localiztion States of YFP-STIM1 Regulated By Ca²⁺ Binding

Figure 4:
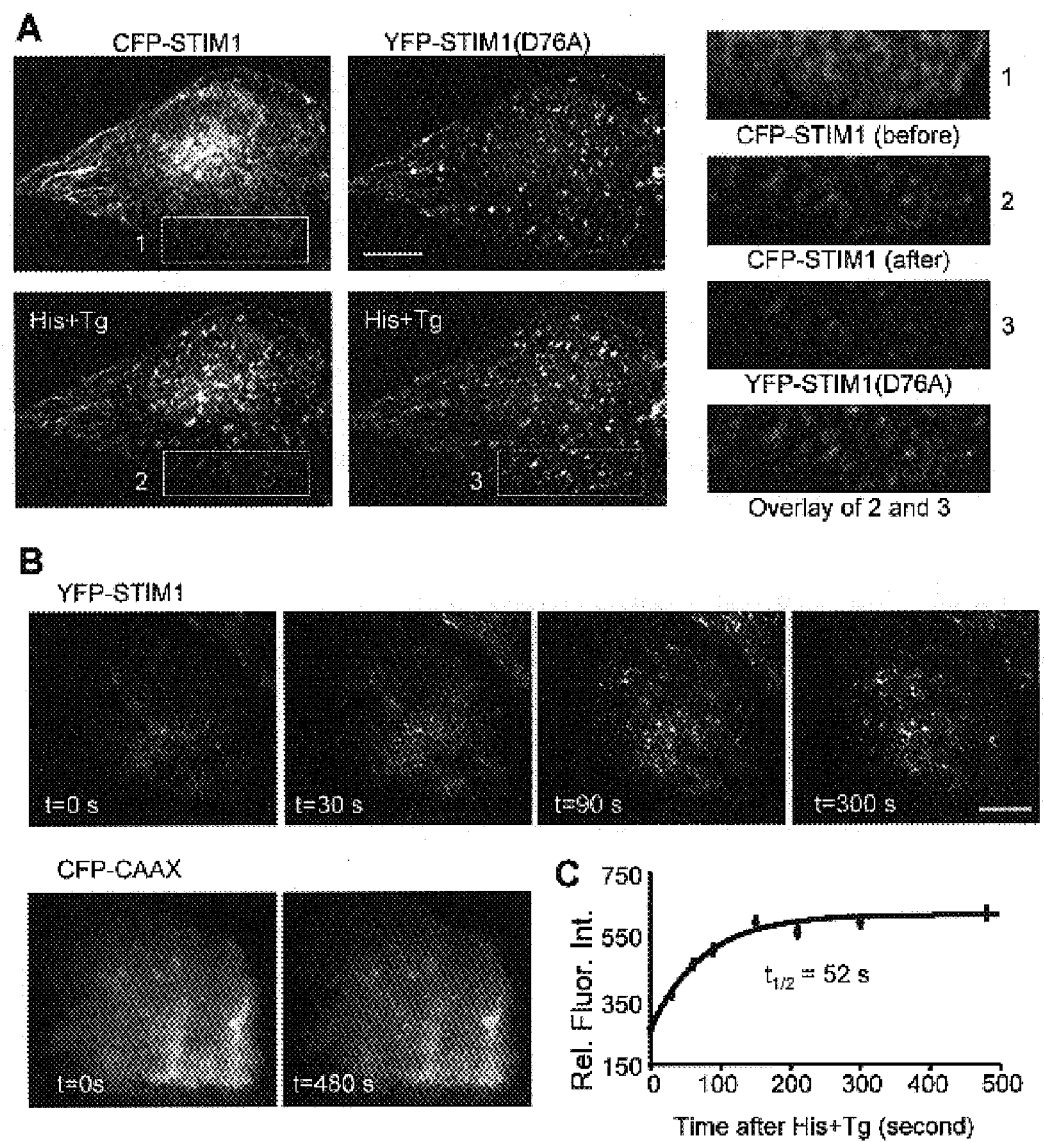
FIG. 4 is a set of photographs and a graph showing that STIM1 exists in two localization states and is rapidly redistributed into puncta near the plasma membrane following Ca$^{2+}$ store depletion. Panel A: Co-localization of wild-type and the EF-mutant of STIM1 in puncta following Ca$^{2+}$ store depletion. HeLa cells were co-transfected with CFP-STIM1 and YFP-STIM1(D76A). CFP/YFP confocal images were taken near the adhesion surface of the same cell before (top two panels) and 2.5 minutes after (bottom two panels) histamine plus thapsigargin stimulation. The magnified panels on the right show STIM1 puncta formation and the co-localization of wild-type and the EF-hand mutant of STIM1 following Ca$^{2+}$ store depletion. Panel B: TIRF microcopy shows that many YFP-STIM1 puncta are rapidly formed within 100 nm of the plasma membrane. HeLa cells were co-transfected with YFP-STIM1 and CFP-CAAX. CFP/YFP TIRF images were taken in the same cells at different time points following histamine plus thapsigargin stimulation. Scale bar=-10 μm. Panel C: Kinetic analysis of the average relative fluorescence intensity in near plasma membrane YFP-STIM1 puncta (n=212; an exponential fit is shown).

A CFP-conjugated wild-type STIM1 that can be imaged in the same cell as the YFP-conjugated STIM1 EF-hand mutant was constructed in order to directly compare the puncta formed by wild-type and the EF-hand mutant of STIM1. The cells were monitored by confocal microscopy, focusing near the cell adhesion surface where the largest numbers of puncta formed by the EF-hand mutant could be seen. Remarkably, store depletion triggered a translocation of the initially ER-distributed wild-type STIM1 into the same puncta already marked by the EF-hand mutant (FIG. 4, Panel A). This suggests that STIM can exist in two states, a relatively uniform ER distribution when Ca²⁺ is bound and a punctate distribution when Ca²⁺ dissociates or when the EF-hand Ca²⁺-binding site is mutated.

Example 8

Rapid Redistribution of YFP-STIM1 Into Puncta Near the Plasma Membrane

An "induced coupling" model has been proposed previously for activation of plasma membrane SOC channels (Venkatachalam et al., (2003) Nat. Cell Biol. 4, E263-72) in which Ca²⁺ store depletion may induce the formation of new conformationally coupled junctions between ER and the plasma membrane. To investigate whether some of the STIM1 puncta are formed near the plasma membrane following Ca²⁺ store depletion, total internal reflection fluorescence (TIRF) microscopy was used to selectively excite fluorescence within 100 nm of the plasma membrane (Steyer et al., (2001) Nat. Rev. Mol. Cell Biol. 2, 268-75), and STIM1 puncta formation was measured. Comparing YFP-STIM1 to a CFP-conjugated plasma membrane marker, CFP-CAAX, in the same cell using TIRF microscopy, reveals a fast increase in near plasma membrane punctate fluorescence intensity following Ca²⁺ store depletion (FIG. 4, Panel B). The kinetics of YFP-STIM1 puncta formation near the plasma membrane (t1/2=52 seconds, FIG. 4, Panel C) are also consistent with previously reported times required for the activation of SOC influx (tens or hundreds of seconds (Steyer et al., (2001) Nat. Rev. Mol. Cell Biol. 2, 268-75). While the resolution of the TIRF measurements cannot definitely prove that there is a physical link between STIM and the plasma membrane, they show that a fraction of the puncta rapidly form within 100 nm of the plasma membrane. This is consistent with a hypothesis that short-range signaling or direct coupling might be involved in the activation of SOC influx pathway by STIM proteins.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of detecting intracellular calcium store levels in a cell, the method comprising:
    detecting a calcium biosensor polypeptide (CBP) distribution pattern in a cell comprising the CBP, wherein the CBP comprises a detectable domain operably linked to a stromal interaction molecule (STIM) polypeptide, wherein the STIM polypeptide comprises, from N-terminus to C-terminus, an EF-hand domain, a sterile alpha motif (SAM) domain, a transmembrane domain, and an ezrin-radixin-moesin (ERM) domain, wherein said EF-hand domain, SAM domain, transmembrane domain, and ERM domain are each of mammalian origin, by detecting a pattern of a detectable signal of the detectable domain in the cell;
    wherein the CBP distribution pattern is indicative of intracellular calcium store levels in the cell.

2. The method according to claim 1, wherein the detectable domain is a fluorescent polypeptide.

3. The method according to claim 1, wherein a punctate CBP distribution pattern is indicative of depletion of intracellular store calcium.

4. The method according to claim 1, wherein a diffuse CBP distribution pattern is indicative of levels of intracellular store calcium that are not depleted.

5. The method of claim 1, wherein the STIM polypeptide is a STIM1 polypeptide comprising from N-terminus to C-terminus of SEQ ID NO:3, an EF-hand domain of amino acids 67-95, a SAM domain of amino acids 130-199, a transmembrane domain of amino acids 214-232, and an ERM domain of amino acids 253-424.

6. The method of claim 1, wherein the STIM polypeptide is a STIM2 polypeptide comprising from N-terminus to C-terminus of SEQ ID NO:4, an EF-hand domain of amino acids 158-186, a SAM domain of amino acids 222-290, a transmembrane domain of amino acids 305-323, and an ERM domain of amino acids 344-515.

7. The method of claim 1 further comprising:

detecting a calcium insensitive marker (CIM) polypeptide distribution pattern in a cell comprising the CIM polypeptide, wherein the CIM polypeptide comprises a detectable domain operably linked to a stromal interaction molecule (STIM) polypeptide, wherein the STIM polypeptide comprises, from N-terminus to C-terminus, a calcium-insensitive EF-hand domain, a sterile alpha motif (SAM) domain, a transmembrane domain and an ezrin-radixin-moesin (ERM) domain, wherein the detectable domain provides a detectable signal different from the detectable signal of the CBP, and wherein said EF-hand domain, SAM domain, transmembrane domain, and ERM domain are each of mammalian origin.

8. The method of claim 1, wherein the detectable domain is immunodetectable.

9. The method of claim 1, wherein the cell is fixed prior to the detecting.

10. The method of claim 1, wherein the detecting is of different time points.

11. The method of claim 1, wherein the detecting is in real time.

* * * * *

UNITED STATES PATENT AND TRADEMARK OFFICE
CERTIFICATE OF CORRECTION

PATENT NO. : 7,481,994 B2
APPLICATION NO. : 11/446010
DATED : January 27, 2009
INVENTOR(S) : Liou et al.

Page 1 of 1

It is certified that error appears in the above-identified patent and that said Letters Patent is hereby corrected as shown below:

In the Specification:

Column 1, line no. 12-18 should read--

--FEDERALLY-SPONSORED RESEARCH OR DEVELOPMENT
This invention was made with Government support under contracts GM030179, CA083229, and GM063702 awarded by the National Institutes of Health. The Government has certain rights in this invention.--

Signed and Sealed this
Thirtieth Day of April, 2013

Teresa Stanek Rea
*Acting Director of the United States Patent and Trademark Office*

SEQUENCE LISTING

```
<160> NUMBER OF SEQ ID NOS: 5

<210> SEQ ID NO 1
<211> LENGTH: 2829
<212> TYPE: DNA
<213> ORGANISM: Artificial Sequence
<220> FEATURE:
<223> OTHER INFORMATION: fusion protein
<220> FEATURE:
<221> NAME/KEY: CDS
<222> LOCATION: (1)...(2829)

<400> SEQUENCE: 1 atg gat gta tgc gtc cgt ctt gcc ctg tgg ctc ctc tgg gga ctc ctc      48
Met Asp Val Cys Val Arg Leu Ala Leu Trp Leu Leu Trp Gly Leu Leu
 1               5                  10                  15 ctg cac cag ggc cag agc ctc gca ccg gtc gcc acc atg gtg agc aag      96
```

-continued

| | | |
|---|---|---|
| Leu His Gln Gly Gln Ser Leu Ala Pro Val Ala Thr Met Val Ser Lys<br>20                  25                  30 | | |
| ggc gag gag ctg ttc acc ggg gtg gtg ccc atc ctg gtc gag ctg gac<br>Gly Glu Glu Leu Phe Thr Gly Val Val Pro Ile Leu Val Glu Leu Asp<br>            35                  40                  45 | | 144 |
| ggc gac gta aac ggc cac aag ttc agc gtg tcc ggc gag ggc gag ggc<br>Gly Asp Val Asn Gly His Lys Phe Ser Val Ser Gly Glu Gly Glu Gly<br>    50                  55                  60 | | 192 |
| gat gcc acc tac ggc aag ctg acc ctg aag ttc atc tgc acc acc ggc<br>Asp Ala Thr Tyr Gly Lys Leu Thr Leu Lys Phe Ile Cys Thr Thr Gly<br>65                  70                  75                  80 | | 240 |
| aag ctg ccc gtg ccc tgg ccc acc ctc gtg acc acc ttc ggc tac ggc<br>Lys Leu Pro Val Pro Trp Pro Thr Leu Val Thr Thr Phe Gly Tyr Gly<br>                85                  90                  95 | | 288 |
| ctg cag tgc ttc gcc cgc tac ccc gac cac atg aag cag cac gac ttc<br>Leu Gln Cys Phe Ala Arg Tyr Pro Asp His Met Lys Gln His Asp Phe<br>        100                 105                 110 | | 336 |
| ttc aag tcc gcc atg ccc gaa ggc tac gtc cag gag cgc acc atc ttc<br>Phe Lys Ser Ala Met Pro Glu Gly Tyr Val Gln Glu Arg Thr Ile Phe<br>    115                 120                 125 | | 384 |
| ttc aag gac gac ggc aac tac aag acc cgc gcc gag gtg aag ttc gag<br>Phe Lys Asp Asp Gly Asn Tyr Lys Thr Arg Ala Glu Val Lys Phe Glu<br>130                 135                 140 | | 432 |
| ggc gac acc ctg gtg aac cgc atc gag ctg aag ggc atc gac ttc aag<br>Gly Asp Thr Leu Val Asn Arg Ile Glu Leu Lys Gly Ile Asp Phe Lys<br>145                 150                 155                 160 | | 480 |
| gag gac ggc aac atc ctg ggg cac aag ctg gag tac aac tac aac agc<br>Glu Asp Gly Asn Ile Leu Gly His Lys Leu Glu Tyr Asn Tyr Asn Ser<br>                165                 170                 175 | | 528 |
| cac aac gtc tat atc atg gcc gac aag cag aag aac ggc atc aag gtg<br>His Asn Val Tyr Ile Met Ala Asp Lys Gln Lys Asn Gly Ile Lys Val<br>        180                 185                 190 | | 576 |
| aac ttc aag atc cgc cac aac atc gag gac ggc agc gtg cag ctc gcc<br>Asn Phe Lys Ile Arg His Asn Ile Glu Asp Gly Ser Val Gln Leu Ala<br>    195                 200                 205 | | 624 |
| gac cac tac cag cag aac acc ccc atc ggc gac ggc ccc gtg ctg ctg<br>Asp His Tyr Gln Gln Asn Thr Pro Ile Gly Asp Gly Pro Val Leu Leu<br>210                 215                 220 | | 672 |
| ccc gac aac cac tac ctg agc tac cag tcc gcc ctg agc aaa gac ccc<br>Pro Asp Asn His Tyr Leu Ser Tyr Gln Ser Ala Leu Ser Lys Asp Pro<br>225                 230                 235                 240 | | 720 |
| aac gag aag cgc gat cac atg gtc ctg ctg gag ttc gtg acc gcc gcc<br>Asn Glu Lys Arg Asp His Met Val Leu Leu Glu Phe Val Thr Ala Ala<br>                245                 250                 255 | | 768 |
| ggg atc act ctc ggc atg gac gag ctg tac aag tcc gga tca aca agt<br>Gly Ile Thr Leu Gly Met Asp Glu Leu Tyr Lys Ser Gly Ser Thr Ser<br>        260                 265                 270 | | 816 |
| ttg tac aaa aaa gca ggc tcc ctc agc cat agt cac agt gag aag gcg<br>Leu Tyr Lys Lys Ala Gly Ser Leu Ser His Ser His Ser Glu Lys Ala<br>    275                 280                 285 | | 864 |
| aca gga acc agc tcg ggg gcc aac tct gag gag tcc act gca gca gag<br>Thr Gly Thr Ser Ser Gly Ala Asn Ser Glu Glu Ser Thr Ala Ala Glu<br>290                 295                 300 | | 912 |
| ttt tgc cga att gac aag ccc ctg tgt cac agt gag gat gag aaa ctc<br>Phe Cys Arg Ile Asp Lys Pro Leu Cys His Ser Glu Asp Glu Lys Leu<br>305                 310                 315                 320 | | 960 |
| agc ttc gag gca gtc cgt aac atc cac aaa ctg atg gac gat gat gcc<br>Ser Phe Glu Ala Val Arg Asn Ile His Lys Leu Met Asp Asp Asp Ala<br>                325                 330                 335 | | 1008 |

-continued

| | |
|---|---|
| aat ggt gat gtg gat gtg gaa gaa agt gat gag ttc ctg agg gaa gac<br>Asn Gly Asp Val Asp Val Glu Glu Ser Asp Glu Phe Leu Arg Glu Asp<br>340 345 350 | 1056 |
| ctc aat tac cat gac cca aca gtg aaa cac agc acc ttc cat ggt gag<br>Leu Asn Tyr His Asp Pro Thr Val Lys His Ser Thr Phe His Gly Glu<br>355 360 365 | 1104 |
| gat aag ctc atc agc gtg gag gac ctg tgg aag gca tgg aag tca tca<br>Asp Lys Leu Ile Ser Val Glu Asp Leu Trp Lys Ala Trp Lys Ser Ser<br>370 375 380 | 1152 |
| gaa gta tac aat tgg acc gtg gat gag gtg gta cag tgg ctg atc aca<br>Glu Val Tyr Asn Trp Thr Val Asp Glu Val Val Gln Trp Leu Ile Thr<br>385 390 395 400 | 1200 |
| tat gtg gag ctg cct cag tat gag gag acc ttc cgg aag ctg cag ctc<br>Tyr Val Glu Leu Pro Gln Tyr Glu Glu Thr Phe Arg Lys Leu Gln Leu<br>405 410 415 | 1248 |
| agt ggc cat gcc atg cca agg ctg gct gtc acc aac acc atg aca<br>Ser Gly His Ala Met Pro Arg Leu Ala Val Thr Asn Thr Thr Met Thr<br>420 425 430 | 1296 |
| ggg act gtg ctg aag atg aca gac cgg agt cat cgg cag aag ctg cag<br>Gly Thr Val Leu Lys Met Thr Asp Arg Ser His Arg Gln Lys Leu Gln<br>435 440 445 | 1344 |
| ctg aag gct ctg gat aca gtg ctc ttt ggg cct cct ctc ttg act cgc<br>Leu Lys Ala Leu Asp Thr Val Leu Phe Gly Pro Pro Leu Leu Thr Arg<br>450 455 460 | 1392 |
| cat aat cac ctc aag gac ttc atg ctg gtg gtg tct atc gtt att ggt<br>His Asn His Leu Lys Asp Phe Met Leu Val Val Ser Ile Val Ile Gly<br>465 470 475 480 | 1440 |
| gtg ggc ggc tgc tgg ttt gcc tat atc cag aac cgt tac tcc aag gag<br>Val Gly Gly Cys Trp Phe Ala Tyr Ile Gln Asn Arg Tyr Ser Lys Glu<br>485 490 495 | 1488 |
| cac atg aag aag atg atg aag gac ttg gag ggg tta cac cga gct gag<br>His Met Lys Lys Met Met Lys Asp Leu Glu Gly Leu His Arg Ala Glu<br>500 505 510 | 1536 |
| cag agt ctg cat gac ctt cag gaa agg ctg cac aag gcc cag gag gag<br>Gln Ser Leu His Asp Leu Gln Glu Arg Leu His Lys Ala Gln Glu Glu<br>515 520 525 | 1584 |
| cac cgc aca gtg gag gtg gag aag gtc cat ctg gaa aag aag ctg cgc<br>His Arg Thr Val Glu Val Glu Lys Val His Leu Glu Lys Lys Leu Arg<br>530 535 540 | 1632 |
| gat gag atc aac ctt gct aag cag gaa gcc cag cgg ctg aag gag ctg<br>Asp Glu Ile Asn Leu Ala Lys Gln Glu Ala Gln Arg Leu Lys Glu Leu<br>545 550 555 560 | 1680 |
| cgg gag ggt act gag aat gag cgg agc cgc caa aaa tat gct gag gag<br>Arg Glu Gly Thr Glu Asn Glu Arg Ser Arg Gln Lys Tyr Ala Glu Glu<br>565 570 575 | 1728 |
| gag ttg gag cag gtt cgg gag gcc ttg agg aaa gca gag aag gag cta<br>Glu Leu Glu Gln Val Arg Glu Ala Leu Arg Lys Ala Glu Lys Glu Leu<br>580 585 590 | 1776 |
| gaa tct cac agc tca tgg tat gct cca gag gcc ctt cag aag tgg ctg<br>Glu Ser His Ser Ser Trp Tyr Ala Pro Glu Ala Leu Gln Lys Trp Leu<br>595 600 605 | 1824 |
| cag ctg aca cat gag gtg gag gtg caa tat tac aac atc aag aag caa<br>Gln Leu Thr His Glu Val Glu Val Gln Tyr Tyr Asn Ile Lys Lys Gln<br>610 615 620 | 1872 |
| aat gct gag aag cag ctg ctg gtg gcc aag gag ggg gct gag aag ata<br>Asn Ala Glu Lys Gln Leu Leu Val Ala Lys Glu Gly Ala Glu Lys Ile<br>625 630 635 640 | 1920 |
| aaa aag aag aga aac aca ctc ttt ggc acc ttc cac gtg gcc cac agc<br>Lys Lys Lys Arg Asn Thr Leu Phe Gly Thr Phe His Val Ala His Ser<br>645 650 655 | 1968 |

| | | | | | | | | | | | | | | | | |
|---|---|---|---|---|---|---|---|---|---|---|---|---|---|---|---|---|
| tct | tcc | ctg | gat | gat | gta | gat | cat | aaa | att | cta | aca | gct | aag | caa | gca | 2016 |
| Ser | Ser | Leu | Asp | Asp | Val | Asp | His | Lys | Ile | Leu | Thr | Ala | Lys | Gln | Ala | |
| | | | 660 | | | | | 665 | | | | | 670 | | | |

| | | | | | | | | | | | | | | | | |
|---|---|---|---|---|---|---|---|---|---|---|---|---|---|---|---|---|
| ctg | agc | gag | gtg | aca | gca | gca | ttg | cgg | gag | cgc | ctg | cac | cgc | tgg | caa | 2064 |
| Leu | Ser | Glu | Val | Thr | Ala | Ala | Leu | Arg | Glu | Arg | Leu | His | Arg | Trp | Gln | |
| | | 675 | | | | | 680 | | | | | 685 | | | | |

| | | | | | | | | | | | | | | | | |
|---|---|---|---|---|---|---|---|---|---|---|---|---|---|---|---|---|
| cag | atc | gag | atc | ctc | tgt | ggc | ttc | cag | att | gtc | aac | aac | cct | ggc | atc | 2112 |
| Gln | Ile | Glu | Ile | Leu | Cys | Gly | Phe | Gln | Ile | Val | Asn | Asn | Pro | Gly | Ile | |
| 690 | | | | | 695 | | | | | 700 | | | | | | |

| | | | | | | | | | | | | | | | | |
|---|---|---|---|---|---|---|---|---|---|---|---|---|---|---|---|---|
| cac | tca | ctg | gtg | gct | gcc | ctc | aac | ata | gac | ccc | agc | tgg | atg | ggc | agt | 2160 |
| His | Ser | Leu | Val | Ala | Ala | Leu | Asn | Ile | Asp | Pro | Ser | Trp | Met | Gly | Ser | |
| 705 | | | | 710 | | | | | 715 | | | | | 720 | | |

| | | | | | | | | | | | | | | | | |
|---|---|---|---|---|---|---|---|---|---|---|---|---|---|---|---|---|
| aca | cgc | ccc | aac | cct | gct | cac | ttc | atc | atg | act | gac | gac | gtg | gat | gac | 2208 |
| Thr | Arg | Pro | Asn | Pro | Ala | His | Phe | Ile | Met | Thr | Asp | Asp | Val | Asp | Asp | |
| | | | 725 | | | | | 730 | | | | | 735 | | | |

| | | | | | | | | | | | | | | | | |
|---|---|---|---|---|---|---|---|---|---|---|---|---|---|---|---|---|
| atg | gat | gag | gag | att | gtg | tct | ccc | ttg | tcc | atg | cag | tcc | cct | agc | ctg | 2256 |
| Met | Asp | Glu | Glu | Ile | Val | Ser | Pro | Leu | Ser | Met | Gln | Ser | Pro | Ser | Leu | |
| | | 740 | | | | | 745 | | | | | 750 | | | | |

| | | | | | | | | | | | | | | | | |
|---|---|---|---|---|---|---|---|---|---|---|---|---|---|---|---|---|
| cag | agc | agt | gtt | cgg | cag | cgc | ctg | acg | gag | cca | cag | cat | ggc | ctg | gga | 2304 |
| Gln | Ser | Ser | Val | Arg | Gln | Arg | Leu | Thr | Glu | Pro | Gln | His | Gly | Leu | Gly | |
| | | | | 755 | | | | | 760 | | | | | 765 | | |

| | | | | | | | | | | | | | | | | |
|---|---|---|---|---|---|---|---|---|---|---|---|---|---|---|---|---|
| tct | cag | agg | gat | ttg | acc | cat | tcc | gat | tcg | gag | tcc | tcc | ctc | cac | atg | 2352 |
| Ser | Gln | Arg | Asp | Leu | Thr | His | Ser | Asp | Ser | Glu | Ser | Ser | Leu | His | Met | |
| 770 | | | | | 775 | | | | | 780 | | | | | | |

| | | | | | | | | | | | | | | | | |
|---|---|---|---|---|---|---|---|---|---|---|---|---|---|---|---|---|
| agt | gac | cgc | cag | cgt | gtg | gcc | ccc | aaa | cct | cct | cag | atg | agc | cgt | gct | 2400 |
| Ser | Asp | Arg | Gln | Arg | Val | Ala | Pro | Lys | Pro | Pro | Gln | Met | Ser | Arg | Ala | |
| 785 | | | | 790 | | | | | 795 | | | | | 800 | | |

| | | | | | | | | | | | | | | | | |
|---|---|---|---|---|---|---|---|---|---|---|---|---|---|---|---|---|
| gca | gac | gag | gct | ctc | aat | gcc | atg | act | tcc | aat | ggc | agc | cac | cgg | ctg | 2448 |
| Ala | Asp | Glu | Ala | Leu | Asn | Ala | Met | Thr | Ser | Asn | Gly | Ser | His | Arg | Leu | |
| | | | | 805 | | | | | 810 | | | | | 815 | | |

| | | | | | | | | | | | | | | | | |
|---|---|---|---|---|---|---|---|---|---|---|---|---|---|---|---|---|
| atc | gag | ggg | gtc | cac | cca | ggg | tct | ctg | gtg | gag | aaa | ctg | cct | gac | agc | 2496 |
| Ile | Glu | Gly | Val | His | Pro | Gly | Ser | Leu | Val | Glu | Lys | Leu | Pro | Asp | Ser | |
| | | | 820 | | | | | 825 | | | | | 830 | | | |

| | | | | | | | | | | | | | | | | |
|---|---|---|---|---|---|---|---|---|---|---|---|---|---|---|---|---|
| cct | gcc | ctg | gcc | aag | aag | gca | tta | ctg | gcg | ctg | aac | cat | ggg | ctg | gac | 2544 |
| Pro | Ala | Leu | Ala | Lys | Lys | Ala | Leu | Leu | Ala | Leu | Asn | His | Gly | Leu | Asp | |
| | | 835 | | | | | 840 | | | | | 845 | | | | |

| | | | | | | | | | | | | | | | | |
|---|---|---|---|---|---|---|---|---|---|---|---|---|---|---|---|---|
| aag | gcc | cac | agc | ctg | atg | gag | ctg | agc | ccc | tca | gcc | cca | cct | ggt | ggc | 2592 |
| Lys | Ala | His | Ser | Leu | Met | Glu | Leu | Ser | Pro | Ser | Ala | Pro | Pro | Gly | Gly | |
| 850 | | | | | 855 | | | | | 860 | | | | | | |

| | | | | | | | | | | | | | | | | |
|---|---|---|---|---|---|---|---|---|---|---|---|---|---|---|---|---|
| tct | cca | cat | ttg | gat | tct | tcc | cgt | tct | cac | agc | ccc | agc | tcc | cca | gac | 2640 |
| Ser | Pro | His | Leu | Asp | Ser | Ser | Arg | Ser | His | Ser | Pro | Ser | Ser | Pro | Asp | |
| 865 | | | | 870 | | | | | 875 | | | | | 880 | | |

| | | | | | | | | | | | | | | | | |
|---|---|---|---|---|---|---|---|---|---|---|---|---|---|---|---|---|
| cca | gac | aca | cca | tct | cca | gtt | ggg | gac | agc | cga | gcc | ctg | caa | gcc | agc | 2688 |
| Pro | Asp | Thr | Pro | Ser | Pro | Val | Gly | Asp | Ser | Arg | Ala | Leu | Gln | Ala | Ser | |
| | | | | 885 | | | | | 890 | | | | | 895 | | |

| | | | | | | | | | | | | | | | | |
|---|---|---|---|---|---|---|---|---|---|---|---|---|---|---|---|---|
| cga | aac | aca | cgc | att | ccc | cac | ctg | gct | ggc | aag | aag | gct | gtg | gct | gag | 2736 |
| Arg | Asn | Thr | Arg | Ile | Pro | His | Leu | Ala | Gly | Lys | Lys | Ala | Val | Ala | Glu | |
| | | | 900 | | | | | 905 | | | | | 910 | | | |

| | | | | | | | | | | | | | | | | |
|---|---|---|---|---|---|---|---|---|---|---|---|---|---|---|---|---|
| gag | gat | aat | ggc | tct | att | ggc | gag | gaa | aca | gac | tcc | agc | cca | ggc | cgg | 2784 |
| Glu | Asp | Asn | Gly | Ser | Ile | Gly | Glu | Glu | Thr | Asp | Ser | Ser | Pro | Gly | Arg | |
| | | 915 | | | | | 920 | | | | | 925 | | | | |

| | | | | | | | | | | | | | |
|---|---|---|---|---|---|---|---|---|---|---|---|---|---|
| aag | aag | ttt | cct | ctc | aaa | atc | ttt | aag | aag | cct | ctt | aag | aag tag | 2829 |
| Lys | Lys | Phe | Pro | Leu | Lys | Ile | Phe | Lys | Lys | Pro | Leu | Lys | Lys * | |
| 930 | | | | | 935 | | | | | 940 | | | | |

<210> SEQ ID NO 2
<211> LENGTH: 942
<212> TYPE: PRT
<213> ORGANISM: Artificial Sequence
<220> FEATURE:

<223> OTHER INFORMATION: fusion protein

<400> SEQUENCE: 2

```
Met Asp Val Cys Val Arg Leu Ala Leu Trp Leu Leu Trp Gly Leu Leu
1               5                   10                  15

Leu His Gln Gly Gln Ser Leu Ala Pro Val Ala Thr Met Val Ser Lys
            20                  25                  30

Gly Glu Glu Leu Phe Thr Gly Val Val Pro Ile Leu Val Glu Leu Asp
        35                  40                  45

Gly Asp Val Asn Gly His Lys Phe Ser Val Ser Gly Glu Gly Glu Gly
    50                  55                  60

Asp Ala Thr Tyr Gly Lys Leu Thr Leu Lys Phe Ile Cys Thr Thr Gly
65                  70                  75                  80

Lys Leu Pro Val Pro Trp Pro Thr Leu Val Thr Thr Phe Gly Tyr Gly
                85                  90                  95

Leu Gln Cys Phe Ala Arg Tyr Pro Asp His Met Lys Gln His Asp Phe
            100                 105                 110

Phe Lys Ser Ala Met Pro Glu Gly Tyr Val Gln Glu Arg Thr Ile Phe
        115                 120                 125

Phe Lys Asp Asp Gly Asn Tyr Lys Thr Arg Ala Glu Val Lys Phe Glu
    130                 135                 140

Gly Asp Thr Leu Val Asn Arg Ile Glu Leu Lys Gly Ile Asp Phe Lys
145                 150                 155                 160

Glu Asp Gly Asn Ile Leu Gly His Lys Leu Glu Tyr Asn Tyr Asn Ser
                165                 170                 175

His Asn Val Tyr Ile Met Ala Asp Lys Gln Lys Asn Gly Ile Lys Val
            180                 185                 190

Asn Phe Lys Ile Arg His Asn Ile Glu Asp Gly Ser Val Gln Leu Ala
        195                 200                 205

Asp His Tyr Gln Gln Asn Thr Pro Ile Gly Asp Gly Pro Val Leu Leu
    210                 215                 220

Pro Asp Asn His Tyr Leu Ser Tyr Gln Ser Ala Leu Ser Lys Asp Pro
225                 230                 235                 240

Asn Glu Lys Arg Asp His Met Val Leu Leu Glu Phe Val Thr Ala Ala
                245                 250                 255

Gly Ile Thr Leu Gly Met Asp Glu Leu Tyr Lys Ser Gly Ser Thr Ser
            260                 265                 270

Leu Tyr Lys Lys Ala Gly Ser Leu Ser His Ser His Ser Glu Lys Ala
        275                 280                 285

Thr Gly Thr Ser Ser Gly Ala Asn Ser Glu Glu Ser Thr Ala Ala Glu
    290                 295                 300

Phe Cys Arg Ile Asp Lys Pro Leu Cys His Ser Glu Asp Glu Lys Leu
305                 310                 315                 320

Ser Phe Glu Ala Val Arg Asn Ile His Lys Leu Met Asp Asp Asp Ala
                325                 330                 335

Asn Gly Asp Val Asp Val Glu Glu Ser Asp Glu Phe Leu Arg Glu Asp
            340                 345                 350

Leu Asn Tyr His Asp Pro Thr Val Lys His Ser Thr Phe His Gly Glu
        355                 360                 365

Asp Lys Leu Ile Ser Val Glu Asp Leu Trp Lys Ala Trp Lys Ser Ser
    370                 375                 380

Glu Val Tyr Asn Trp Thr Val Asp Glu Val Val Gln Trp Leu Ile Thr
385                 390                 395                 400
```

-continued

```
Tyr Val Glu Leu Pro Gln Tyr Glu Thr Phe Arg Lys Leu Gln Leu
            405                 410                 415
Ser Gly His Ala Met Pro Arg Leu Ala Val Thr Asn Thr Thr Met Thr
        420                 425                 430
Gly Thr Val Leu Lys Met Thr Asp Arg Ser His Arg Gln Lys Leu Gln
            435                 440                 445
Leu Lys Ala Leu Asp Thr Val Leu Phe Gly Pro Pro Leu Leu Thr Arg
    450                 455                 460
His Asn His Leu Lys Asp Phe Met Leu Val Val Ser Ile Val Ile Gly
465                 470                 475                 480
Val Gly Gly Cys Trp Phe Ala Tyr Ile Gln Asn Arg Tyr Ser Lys Glu
                485                 490                 495
His Met Lys Lys Met Met Lys Asp Leu Glu Gly Leu His Arg Ala Glu
            500                 505                 510
Gln Ser Leu His Asp Leu Gln Glu Arg Leu His Lys Ala Gln Glu Glu
        515                 520                 525
His Arg Thr Val Glu Val Glu Lys Val His Leu Glu Lys Lys Leu Arg
    530                 535                 540
Asp Glu Ile Asn Leu Ala Lys Gln Glu Ala Gln Arg Leu Lys Glu Leu
545                 550                 555                 560
Arg Glu Gly Thr Glu Asn Glu Arg Ser Arg Gln Lys Tyr Ala Glu Glu
                565                 570                 575
Glu Leu Glu Gln Val Arg Glu Ala Leu Arg Lys Ala Glu Lys Glu Leu
            580                 585                 590
Glu Ser His Ser Ser Trp Tyr Ala Pro Glu Ala Leu Gln Lys Trp Leu
        595                 600                 605
Gln Leu Thr His Glu Val Glu Val Gln Tyr Tyr Asn Ile Lys Lys Gln
    610                 615                 620
Asn Ala Glu Lys Gln Leu Leu Val Ala Lys Glu Gly Ala Glu Lys Ile
625                 630                 635                 640
Lys Lys Lys Arg Asn Thr Leu Phe Gly Thr Phe His Val Ala His Ser
                645                 650                 655
Ser Ser Leu Asp Asp Val Asp His Lys Ile Leu Thr Ala Lys Gln Ala
            660                 665                 670
Leu Ser Glu Val Thr Ala Ala Leu Arg Glu Arg Leu His Arg Trp Gln
        675                 680                 685
Gln Ile Glu Ile Leu Cys Gly Phe Gln Ile Val Asn Asn Pro Gly Ile
    690                 695                 700
His Ser Leu Val Ala Ala Leu Asn Ile Asp Pro Ser Trp Met Gly Ser
705                 710                 715                 720
Thr Arg Pro Asn Pro Ala His Phe Ile Met Thr Asp Asp Val Asp Asp
                725                 730                 735
Met Asp Glu Glu Ile Val Ser Pro Leu Ser Met Gln Ser Pro Ser Leu
            740                 745                 750
Gln Ser Ser Val Arg Gln Arg Leu Thr Glu Pro Gln His Gly Leu Gly
        755                 760                 765
Ser Gln Arg Asp Leu Thr His Ser Asp Ser Glu Ser Ser Leu His Met
    770                 775                 780
Ser Asp Arg Gln Arg Val Ala Pro Lys Pro Pro Gln Met Ser Arg Ala
785                 790                 795                 800
Ala Asp Glu Ala Leu Asn Ala Met Thr Ser Asn Gly Ser His Arg Leu
                805                 810                 815
Ile Glu Gly Val His Pro Gly Ser Leu Val Glu Lys Leu Pro Asp Ser
```

-continued

```
                820                 825                 830
Pro Ala Leu Ala Lys Ala Leu Leu Ala Leu Asn His Gly Leu Asp
        835                 840                 845

Lys Ala His Ser Leu Met Glu Leu Ser Pro Ser Ala Pro Pro Gly Gly
    850                 855                 860

Ser Pro His Leu Asp Ser Ser Arg Ser His Ser Pro Ser Ser Pro Asp
865                 870                 875                 880

Pro Asp Thr Pro Ser Pro Val Gly Asp Ser Arg Ala Leu Gln Ala Ser
                885                 890                 895

Arg Asn Thr Arg Ile Pro His Leu Ala Gly Lys Lys Ala Val Ala Glu
            900                 905                 910

Glu Asp Asn Gly Ser Ile Gly Glu Glu Thr Asp Ser Ser Pro Gly Arg
        915                 920                 925

Lys Lys Phe Pro Leu Lys Ile Phe Lys Lys Pro Leu Lys Lys
    930                 935                 940

<210> SEQ ID NO 3
<211> LENGTH: 685
<212> TYPE: PRT
<213> ORGANISM: human

<400> SEQUENCE: 3

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Val Gln Trp Leu Ile Thr Tyr
    130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255
```

```
Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
            275                 280                 285

Glu Ile Asn Leu Ala Lys Gln Glu Ala Gln Arg Leu Lys Glu Leu Arg
            290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                    325                 330                 335

Ser His Ser Ser Trp Tyr Ala Pro Glu Ala Leu Gln Lys Trp Leu Gln
                340                 345                 350

Leu Thr His Glu Val Glu Val Gln Tyr Tyr Asn Ile Lys Lys Gln Asn
            355                 360                 365

Ala Glu Lys Gln Leu Leu Val Ala Lys Glu Gly Ala Glu Lys Ile Lys
            370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                    405                 410                 415

Ser Glu Val Thr Ala Ala Leu Arg Glu Arg Leu His Arg Trp Gln Gln
                420                 425                 430

Ile Glu Ile Leu Cys Gly Phe Gln Ile Val Asn Asn Pro Gly Ile His
            435                 440                 445

Ser Leu Val Ala Ala Leu Asn Ile Asp Pro Ser Trp Met Gly Ser Thr
450                 455                 460

Arg Pro Asn Pro Ala His Phe Ile Met Thr Asp Val Asp Asp Met
465                 470                 475                 480

Asp Glu Glu Ile Val Ser Pro Leu Ser Met Gln Ser Pro Ser Leu Gln
                    485                 490                 495

Ser Ser Val Arg Gln Arg Leu Thr Glu Pro Gln His Gly Leu Gly Ser
                500                 505                 510

Gln Arg Asp Leu Thr His Ser Asp Ser Glu Ser Ser Leu His Met Ser
            515                 520                 525

Asp Arg Gln Arg Val Ala Pro Lys Pro Pro Gln Met Ser Arg Ala Ala
            530                 535                 540

Asp Glu Ala Leu Asn Ala Met Thr Ser Asn Gly Ser His Arg Leu Ile
545                 550                 555                 560

Glu Gly Val His Pro Gly Ser Leu Val Glu Lys Leu Pro Asp Ser Pro
                    565                 570                 575

Ala Leu Ala Lys Lys Ala Leu Leu Ala Leu Asn His Gly Leu Asp Lys
                580                 585                 590

Ala His Ser Leu Met Glu Leu Ser Pro Ser Ala Pro Pro Gly Gly Ser
            595                 600                 605

Pro His Leu Asp Ser Ser Arg Ser His Ser Pro Ser Pro Asp Pro
            610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                    645                 650                 655

Asp Asn Gly Ser Ile Gly Glu Glu Thr Asp Ser Ser Pro Gly Arg Lys
                660                 665                 670
```

```
Lys Phe Pro Leu Lys Ile Phe Lys Pro Leu Lys Lys
        675                 680                 685

<210> SEQ ID NO 4
<211> LENGTH: 833
<212> TYPE: PRT
<213> ORGANISM: human

<400> SEQUENCE: 4

Met Asn Ala Ala Gly Ile Arg Ala Pro Glu Ala Gly Ala Asp Gly
 1               5                  10                  15

Thr Arg Leu Ala Pro Gly Gly Ser Pro Cys Leu Arg Arg Gly Arg
             20                  25                  30

Pro Glu Glu Ser Pro Ala Ala Val Val Ala Pro Arg Gly Ala Gly Glu
                 35                  40                  45

Leu Gln Ala Ala Gly Ala Pro Leu Arg Phe His Pro Ala Ser Pro Arg
     50                  55                  60

Arg Leu His Pro Ala Ser Thr Pro Gly Pro Ala Trp Gly Trp Leu Leu
 65                  70                  75                  80

Arg Arg Arg Arg Trp Ala Ala Leu Leu Val Leu Gly Leu Leu Val Ala
                 85                  90                  95

Gly Ala Ala Asp Gly Cys Glu Leu Val Pro Arg His Leu Arg Gly Arg
                100                 105                 110

Arg Ala Thr Gly Ser Ala Ala Thr Ala Ala Ser Ser Pro Ala Ala Ala
            115                 120                 125

Ala Gly Asp Ser Pro Ala Leu Met Thr Asp Pro Cys Met Ser Leu Ser
    130                 135                 140

Pro Pro Cys Phe Thr Glu Glu Asp Arg Phe Ser Leu Glu Ala Leu Gln
145                 150                 155                 160

Thr Ile His Lys Gln Met Asp Asp Lys Asp Gly Gly Ile Glu Val
                165                 170                 175

Glu Glu Ser Asp Glu Phe Ile Arg Glu Asp Met Lys Tyr Lys Asp Ala
                180                 185                 190

Thr Asn Lys His Ser His Leu His Arg Glu Asp Lys His Ile Thr Ile
            195                 200                 205

Glu Asp Leu Trp Lys Arg Trp Lys Thr Ser Glu Val His Asn Trp Thr
    210                 215                 220

Leu Glu Asp Thr Leu Gln Trp Leu Ile Glu Phe Val Glu Leu Pro Gln
225                 230                 235                 240

Tyr Glu Lys Asn Phe Arg Asp Asn Asn Val Lys Gly Thr Thr Leu Pro
                245                 250                 255

Arg Ile Ala Val His Glu Pro Ser Phe Met Ile Ser Gln Leu Lys Ile
            260                 265                 270

Ser Asp Arg Ser His Arg Gln Lys Leu Gln Leu Lys Ala Leu Asp Val
    275                 280                 285

Val Leu Phe Gly Pro Leu Thr Arg Pro Pro His Asn Trp Met Lys Asp
    290                 295                 300

Phe Ile Leu Thr Val Ser Ile Val Ile Gly Val Gly Gly Cys Trp Phe
305                 310                 315                 320

Ala Tyr Thr Gln Asn Lys Thr Ser Lys Glu His Val Ala Lys Met Met
                325                 330                 335

Lys Asp Leu Glu Ser Leu Gln Thr Ala Glu Gln Ser Leu Met Asp Leu
            340                 345                 350

Gln Glu Arg Leu Glu Lys Ala Gln Glu Glu Asn Arg Asn Val Ala Val
    355                 360                 365
```

-continued

```
Glu Lys Gln Asn Leu Glu Arg Lys Met Met Asp Glu Ile Asn Tyr Ala
    370                 375                 380
Lys Glu Glu Ala Cys Arg Leu Arg Glu Leu Arg Glu Gly Ala Glu Cys
385                 390                 395                 400
Glu Leu Ser Arg Arg Gln Tyr Ala Glu Gln Glu Leu Glu Gln Val Arg
                405                 410                 415
Met Ala Leu Lys Lys Ala Glu Lys Glu Phe Glu Leu Arg Ser Ser Trp
            420                 425                 430
Ser Val Pro Asp Ala Leu Gln Lys Trp Leu Gln Leu Thr His Glu Val
        435                 440                 445
Glu Val Gln Tyr Tyr Asn Ile Lys Arg Gln Asn Ala Glu Met Gln Leu
    450                 455                 460
Ala Ile Ala Lys Asp Glu Ala Glu Lys Ile Lys Lys Arg Ser Thr
465                 470                 475                 480
Val Phe Gly Thr Leu His Val Ala His Ser Ser Leu Asp Glu Val
                485                 490                 495
Asp His Lys Ile Leu Glu Ala Lys Ala Leu Ser Glu Leu Thr Thr
            500                 505                 510
Cys Leu Arg Glu Arg Leu Phe Arg Trp Gln Gln Ile Glu Lys Ile Cys
        515                 520                 525
Gly Phe Gln Ile Ala His Asn Ser Gly Leu Pro Ser Leu Thr Ser Ser
    530                 535                 540
Leu Tyr Ser Asp His Ser Trp Val Val Met Pro Arg Val Ser Ile Pro
545                 550                 555                 560
Pro Tyr Pro Ile Ala Gly Val Asp Asp Leu Asp Glu Asp Thr Pro
                565                 570                 575
Pro Ile Val Ser Gln Phe Pro Gly Thr Met Ala Lys Pro Pro Gly Ser
            580                 585                 590
Leu Ala Arg Ser Ser Ser Leu Cys Arg Ser Arg Arg Ser Ile Val Pro
        595                 600                 605
Ser Ser Pro Gln Pro Gln Arg Ala Gln Leu Ala Pro His Ala Pro His
    610                 615                 620
Pro Ser His Pro Arg His Pro His His Pro Gln His Thr Pro His Ser
625                 630                 635                 640
Leu Pro Ser Pro Asp Pro Asp Ile Leu Ser Val Ser Cys Pro Ala
                645                 650                 655
Leu Tyr Arg Asn Glu Glu Glu Glu Ala Ile Tyr Phe Ser Ala Glu
            660                 665                 670
Lys Gln Trp Glu Val Pro Asp Thr Ala Ser Glu Cys Asp Ser Leu Asn
        675                 680                 685
Ser Ser Ile Gly Arg Lys Gln Ser Pro Leu Ser Leu Glu Ile Tyr
    690                 695                 700
Gln Thr Leu Ser Pro Arg Lys Ile Ser Arg Asp Glu Val Ser Leu Glu
705                 710                 715                 720
Asp Ser Ser Arg Gly Asp Ser Pro Val Thr Val Asp Val Ser Trp Gly
                725                 730                 735
Ser Pro Asp Cys Val Gly Leu Thr Glu Thr Lys Ser Met Ile Phe Ser
            740                 745                 750
Pro Ala Ser Lys Val Tyr Asn Gly Ile Leu Glu Lys Ser Cys Ser Met
        755                 760                 765
Asn Gln Leu Ser Ser Gly Ile Pro Val Pro Lys Pro Arg His Thr Ser
    770                 775                 780
```

```
Cys Ser Ser Ala Gly Asn Asp Ser Lys Pro Val Gln Glu Ala Pro Ser
785                 790                 795                 800

Val Ala Arg Ile Ser Ser Ile Pro His Asp Leu Cys His Asn Gly Glu
                805                 810                 815

Lys Ser Lys Lys Pro Ser Lys Ile Lys Ser Leu Phe Lys Lys Lys Ser
            820                 825                 830

Lys

<210> SEQ ID NO 5
<211> LENGTH: 285
<212> TYPE: PRT
<213> ORGANISM: Artificial Sequence
<220> FEATURE:
<223> OTHER INFORMATION: consensus sequence of human STIM1 and human
      stim2
<220> FEATURE:
<221> NAME/KEY: NON_CONS
<222> LOCATION: (3)...(4)
<223> OTHER INFORMATION: Consensus sequence generated by alignment of
      SEQ ID NO:03 and 04.  Spacing between identical residues is
      omitted.
<220> FEATURE:
<221> NAME/KEY: NON_CONS
<222> LOCATION: (4)...(5)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (5)...(6)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (7)...(8)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (8)...(9)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (9)...(10)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (10)...(11)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (11)...(12)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (12)...(13)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (14)...(15)
<223> OTHER INFORMATION: Consensus sequence generated by alignment of
      SEQ ID NO:03 and 04.  Spacing between identical
      residues is omitted.
```

```
<220> FEATURE:
<221> NAME/KEY: NON_CONS
<222> LOCATION: (17)...(18)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (21)...(22)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (22)...(23)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (29)...(30)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (32)...(33)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (33)...(34)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (34)...(35)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (35)...(36)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (36)...(38)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (38)...(39)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (39)...(40)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (42)...(43)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (43)...(44)
<223> OTHER INFORMATION: Consensus sequence generated by alignment of
      SEQ ID NO:03 and 04.  Spacing between identical
      residues is omitted.
<220> FEATURE:
```

```
<221> NAME/KEY: NON_CONS
<222> LOCATION: (48)...(49)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (50)...(51)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (53)...(54)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (56)...(57)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (60)...(61)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (67)...(68)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (69)...(70)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (70)...(71)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (72)...(73)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (74)...(75)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (76)...(77)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (90)...(91)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (95)...(96)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
```

```
<222> LOCATION: (97)...(98)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (100)...(101)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (101)...(102)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (115)...(116)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (117)...(118)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (121)...(122)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (128)...(129)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (129)...(130)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (134)...(135)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (140)...(141)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (145)...(146)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (146)...(147)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (147)...(148)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (150)...(151)
```

```
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (152)...(153)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (153)...(154)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (157)...(158)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (159)...(160)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (161)...(162)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (163)...(164)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (168)...(169)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (170)...(171)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (172)...(173)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (175)...(176)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (181)...(182)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (183)...(184)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (188)...(189)
<223> OTHER INFORMATION: Consensus sequence generated by alignment of
```

```
      SEQ ID NO:03 and 04.  Spacing between identical
      residues is omitted.
<220> FEATURE:
<221> NAME/KEY: NON_CONS
<222> LOCATION: (189)...(190)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (192)...(193)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (193)...(194)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (213)...(214)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (217)...(218)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (219)...(220)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (221)...(222)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (229)...(230)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (230)...(231)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (233)...(234)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (242)...(243)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (248)...(249)
<223> OTHER INFORMATION: Consensus sequence generated by alignment of
      SEQ ID NO:03 and 04.  Spacing between identical
      residues is omitted.
<220> FEATURE:
<221> NAME/KEY: NON_CONS
<222> LOCATION: (250)...(251)
<223> OTHER INFORMATION: Consensus sequence generated by alignment of
      SEQ ID NO:03 and 04.  Spacing between identical
```

```
       residues is omitted.
<220> FEATURE:
<221> NAME/KEY: NON_CONS
<222> LOCATION: (254)...(255)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (255)...(256)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (260)...(261)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (266)...(267)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (271)...(272)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (272)...(273)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (273)...(274)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (275)...(276)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (276)...(277)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (277)...(278)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (279)...(280)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (280)...(281)
<223> OTHER INFORMATION: Consensus sequence generated by alignment of
       SEQ ID NO:03 and 04.  Spacing between identical
       residues is omitted.
<220> FEATURE:
<221> NAME/KEY: NON_CONS
<222> LOCATION: (283)...(284)
<223> OTHER INFORMATION: Consensus sequence generated by alignment of
       SEQ ID NO:03 and 04.  Spacing between identical
       residues is omitted.
```

```
<400> SEQUENCE: 5

Ala Thr Gly Ala Ser Ala Ala Cys Pro Cys Glu Ser Glu Ala Ile His
1               5                  10                 15

Lys Met Asp Asp Asp Gly Val Glu Glu Ser Asp Glu Phe Arg Glu Asp
            20                  25                 30

Tyr Asp Thr Lys His Ser His Glu Asp Lys Ile Glu Asp Leu Trp Lys
            35                  40                 45

Trp Lys Ser Glu Val Asn Trp Thr Gln Trp Leu Ile Val Glu Leu Pro
        50                  55                 60

Gln Tyr Glu Phe Arg Gly Pro Arg Ala Val Leu Lys Asp Arg Ser His
65                  70                  75                 80

Arg Gln Lys Leu Gln Leu Lys Ala Leu Asp Val Leu Phe Gly Pro His
                85                  90                 95

Asn Lys Asp Phe Leu Val Ser Ile Val Ile Gly Val Gly Gly Cys Trp
            100                 105                110

Phe Ala Tyr Gln Asn Ser Lys Glu His Lys Met Met Lys Asp Leu Glu
            115                 120                125

Leu Ala Glu Gln Ser Leu Asp Leu Gln Glu Arg Leu Lys Ala Gln Glu
        130                 135                 140

Glu Arg Val Val Glu Lys Leu Glu Lys Asp Glu Ile Asn Ala Lys Glu
145                 150                 155                160

Ala Arg Leu Glu Leu Arg Glu Gly Glu Glu Ser Arg Tyr Ala Glu Glu
                165                 170                175

Leu Glu Gln Val Arg Ala Leu Lys Ala Glu Lys Glu Glu Ser Ser Trp
            180                 185                 190

Pro Ala Leu Gln Lys Trp Leu Gln Leu Thr His Glu Val Glu Val Gln
            195                 200                 205

Tyr Tyr Asn Ile Lys Gln Asn Ala Glu Gln Leu Ala Lys Ala Glu Lys
            210                 215                 220

Ile Lys Lys Lys Arg Thr Phe Gly Thr His Val Ala His Ser Ser Ser
225                 230                 235                240

Leu Asp Val Asp His Lys Ile Leu Ala Lys Ala Leu Ser Glu Thr Leu
            245                 250                 255

Arg Glu Arg Leu Arg Trp Gln Gln Ile Glu Cys Gly Phe Gln Ile Asn
            260                 265                 270

Gly Ser Leu Leu Asp Ser Trp Arg Val Asp Asp Glu
            275                 280                 285
```